(12) United States Patent
Tian et al.

(10) Patent No.: US 9,121,795 B2
(45) Date of Patent: Sep. 1, 2015

(54) APPARATUS FOR PROCESSING BIOLOGICAL SAMPLES AND METHOD THEREOF

(76) Inventors: Feng Tian, Vienna, VA (US); Daniel Liang Zou, Richmond Hill (CA); Lingyun Ji, Wuhan (CN)

( * ) Notice: Subject to any disclaimer, the term of this patent is extended or adjusted under 35 U.S.C. 154(b) by 190 days.

(21) Appl. No.: 13/879,995

(22) PCT Filed: Oct. 29, 2010

(86) PCT No.: PCT/US2010/054876
§ 371 (c)(1),
(2), (4) Date: Apr. 17, 2013

(87) PCT Pub. No.: WO2012/057801
PCT Pub. Date: May 3, 2012

(65) Prior Publication Data
US 2013/0203072 A1    Aug. 8, 2013

(51) Int. Cl.
*A61B 10/00* (2006.01)
*G01N 1/31* (2006.01)
*G01N 35/00* (2006.01)
*B01L 3/00* (2006.01)
*G01N 35/04* (2006.01)
(Continued)

(52) U.S. Cl.
CPC ............... *G01N 1/31* (2013.01); *B01L 3/5025* (2013.01); *B01L 9/52* (2013.01); *G01N 35/00* (2013.01); *G01N 35/04* (2013.01); *B01L 2300/021* (2013.01); *C12Q 1/68* (2013.01); *G01N 35/0099* (2013.01); *G01N 2035/0477* (2013.01)

(58) Field of Classification Search
CPC .................. G01N 1/36; G01N 2001/2873

USPC .............................................. 422/63–67, 536
See application file for complete search history.

(56) References Cited

U.S. PATENT DOCUMENTS 6,485,690 B1   11/2002   Pfost
6,887,428 B2 *  5/2005   Wernz et al. .................... 422/63
(Continued)

FOREIGN PATENT DOCUMENTS

CN        1088840 C      8/2002
CN        1847822 A      10/2006
(Continued)

OTHER PUBLICATIONS

SIPO PR China, Notice of the First Office Action for Application No. 201080069617.9, mailed Jan. 16, 2014, 11 pages.

*Primary Examiner* — Jyoti Nagpaul
(74) *Attorney, Agent, or Firm* — Feng Tian

(57) ABSTRACT

The present invention provides devices, apparatuses and methods for automated processing of biological samples. This invention provides automated devices and automated methods of sequentially treating a biological sample with processing fluids in more than one washing basin. In some embodiments, the invention provides automated devices and automated methods of western blot processing. In some embodiments, the invention provides automated devices and automated methods of Southern blot processing. In some embodiments, the invention provides automated devices and automated methods of northern blot processing. In some embodiments, the invention provides automated devices and automated methods of staining biomolecules on solid supports. In some embodiments, the invention provides automated devices and automated methods of nucleic acid separation and isolation.

5 Claims, 13 Drawing Sheets

(51) Int. Cl.
  *B01L 9/00* (2006.01)
  *C12Q 1/68* (2006.01)

(56) References Cited

U.S. PATENT DOCUMENTS

| | | |
|---|---|---|
| 7,472,614 B1 | 1/2009 | Kalidindi |
| 2006/0035271 A1 | 2/2006 | McEntee |
| 2006/0173575 A1 | 8/2006 | Lefebvre |
| 2010/0105130 A1 | 4/2010 | Hanafusa et al. |
| 2010/0167943 A1 | 7/2010 | Adey et al. |
| 2010/0182877 A1 | 7/2010 | Chu |

FOREIGN PATENT DOCUMENTS

| | | |
|---|---|---|
| EP | 1321756 A1 | 6/2003 |
| GB | 836746 A | 6/1960 |
| WO | 9719379 A1 | 5/1997 |

* cited by examiner

APPARATUS FOR PROCESSING BIOLOGICAL SAMPLES AND METHOD THEREOF

CROSS REFERENCE TO RELATED APPLICATION

The application is a 35 U.S.C. §371 national stage application of International Patent Application PCT/US2010/054876 (published as WO2012057801), filed Oct. 29, 2010, the contents of which are hereby incorporated by reference in their entirety.

FIELD OF THE INVENTION

The invention generally relates to automated device, automated apparatus and automated method for processing biological samples and more specifically to automated apparatus and method for performing blotting assays, for staining slides, and for extracting nucleic acids.

BACKGROUND OF THE INVENTION

Historically, time-consuming and laborious manual manipulations are part of certain biological assays and lab procedures. Many of these manipulations would be amenable to and benefit from automation. For example, staining of biological material on glass slides requires repeated washing and drying of samples by a scientist or lab technician. Similarly, performing western blot analysis on the bench needs individual attention from a scientist or lab technician, who has to spend hours keeping track of the process and switching solutions manually. In addition, lack of reproducibility and human errors are potential disadvantages of such labor-intensive manual manipulations. It is desirable to replace such manual operations with automation, which would save researchers' valuable time, minimizes operator errors, and increases consistency of experimental results.

Recently automated devices and apparatuses have been developed to automate processing of routine washing and incubation steps, which are required by standard laboratory procedures including western blotting. One example of such automation is the Freedom Rocker™ made by Next Advance. The Freedom Rocker™ is a laboratory platform rocker with a pump and a timer. To operate this apparatus, the user needs to put a membrane, which contains biomolecules to be analyzed, in a tray, place the tray on a shaker platform, store processing reagents in different reservoirs, and automatically dispense reagent into and aspirate reagent from the tray by a pump. The tray is shaken on the shaker platform to ensure sufficient contact between reagents and the membrane in the same tray. One disadvantage of this type of automation is the use of the pump to dispense biological reagents, such as antibody solutions, which could be trapped in the pipelines of the pump and cause contamination or unwanted biological reactions. Another disadvantage is the use of reservoirs to hold biological reagents and the use of tubes to transfer biological reagents from the reservoir to the pump. The dead volume in the reservoirs and tubes would require extra biological reagents to be made available in addition to the amount needed to treat the biological sample in the tray. Certain biological reagents for the bioprocessing, such as antibodies, are either difficult to make or expensive to buy. Therefore, the requirement of extra biological reagents might become a burden for a researcher and a waste of scarce biological reagents.

ProfiBlot™ 48 made by Tecan is another example of western blot processor for automated washing and incubation of strip-based assays. ProfiBlot™ 48 comprises a disposable 48 well tray for sample strips, 3 pumps to dispense and aspirate solutions, 7 reagent bottles and respective delivery tubing, and a control unit. Its operation is similar to that of Freedom Rocker™ made by Next Advance, which involves pumping solutions from reservoirs to each processing container. Therefore, they have similar disadvantages including the use of a pump and the requirement of extra biological reagents.

A third example of automation was disclosed in an international patent application WO2010025302A2 by Life Technology. This patent application WO2010025302A2 described an automated blot processing device. The device stores processing reagents in different reservoirs and allows automatic dispensing and aspiration of bioprocess fluids to a bioprocessing chamber which holds a membrane containing biomolecules to be analyzed. Instead of shaking the sample with fluids, bioprocessing fluids are circulated within the bioprocessing chamber by removing bioprocessing fluids from the chamber via one fluid flow channel and pumping the bioprocessing fluid back to the chamber via a second fluid flow channel. One disadvantage of this device is again the requirement of extra biological reagents due to the employment of reservoirs and tubes to apply biological reagents to the biological sample in the bioprocessing chamber. Another disadvantage is the fixed volume of the bioprocessing chamber for the application of biological reagents and buffers. A smaller volume for the application of biological reagents than that for the application of buffers would decrease the required amount of scarce biological reagents, such as antibodies. The third disadvantage is that the size of the processing chamber limits the size of the membrane to be analyzed.

A fourth example of automated processor for western blot is BlotCycler™ made by Precision Biosystems. The device automatically dispenses and aspirates reagents from multiple trays simultaneously. A tank stores all the washing buffers while smaller chambers contain different antibodies. A fluid distribution technology is used to deliver buffers and antibodies to each processing tray and a shaking mechanism is used during the incubation. Similar to the aforementioned automations, a membrane stays in the same tray during the process.

In all four examples the membrane to be analyzed stays in the same container, be it a tray, a well or a chamber, throughout the whole process. Unwanted mixing of different bioprocessing fluids might occur if part of a previous bioprocessing fluid is trapped in the container when a different bioprocessing fluid is dispersed into the same container. In addition, a large amount of antibodies is needed for the automation since the antibody solutions need to cover the whole surface of the membrane to be processed.

There is still a need in the art for simple, affordable, and easy to use apparatus which allows for automated processing of biological samples. Due to the high cost and limited amount of the biological reagents used as processing fluids in staining and western blot, it would be advantageous to reduce the volume of biological reagents applied without reducing the concentration thereof. One way to accomplish this goal is to add the biological reagents directly to the bioprocessing container without employing extra reservoirs and transferring tubes to hold the biological reagents. Another way is to reduce the volume of the bioprocessing container while maintaining the even distribution of processing fluids over the surface of the membrane. Moreover, conducting different steps of the blotting process in different bioprocessing containers might reduce the chance and the level of contaminations during the process. The invention described here addresses these and related needs.

SUMMARY OF THE INVENTION

The following embodiments and aspects thereof are described and illustrated in conjunction with devices, apparatuses and methods which are meant to be exemplary and illustrative, not limiting in scope.

The present invention provides devices, apparatuses and methods for processing biological samples. The apparatus comprises a housing, a cover, at least one robot assembly which transfers at least one biological sample held in a sample holder to a plurality of washing basins in a removable washing basin assembly, and a control system which controls the operation of the robot assembly according to a predetermined schedule. The operation of the apparatus is characterized in that different steps of the bioprocessing of a biological sample are conducted in different washing basins, whose physical dimensions might be individualized according to the nature and requirement of the assay. Common processing fluids may be preloaded into washing basins to save time for the researcher.

In some embodiments, the volume of at least one washing basin configured to hold a biological reagent is set to be different from the volume of other washing basins configured to hold other biological reagents or buffers.

In some embodiments, a sample holder has a plurality of openings to allow for the free flow of processing fluids into and out of the sample holder. In some embodiments, a biological sample is held in a circular cylinder type sample holder. In some embodiments, a biological sample is held in a folder type sample holder. In some embodiments, a biological sample is held in a rectangular cube type sample container. In some embodiments, a biological sample is held in a bendable sample holder. In some embodiments, the inner surface of a sample holder, which might be in contact with the solid support of a biological sample, contains multiple bumps to prevent the solid support from blocking the openings on the sample holder.

In some embodiments, washing basins are arranged in a circular array on the washing basin assembly. In some embodiments, washing basins are arranged in a linear array on the washing basin assembly, either in a single row or in multiple rows.

In some embodiments, a robot assembly reciprocates a sample holder along the vertical direction inside a washing basin so that processing fluid therein is evenly dispersed over the surface of a biological sample. In some embodiments, a robot assembly rotates a sample holder within a washing basin so that processing fluid therein is evenly dispersed over the surface of a biological sample.

In some embodiments, a robot assembly transfers a sample holder from one washing basin to another washing basin. In some embodiments, a robot assembly includes at least one motor to steer the movement of a sample holder.

In some embodiments, a control system controls the movements of a robot assembly, including a) moving a biological sample to and from a designated washing basin, b) keeping the biological sample in the designated washing basin for a predetermined time, and c) keeping the frequency at which the robotic assembly agitates the biological sample within the designated washing basin.

In some embodiments, a control system receives bioprocessing commands from a programmable control unit. Said programmable control unit comprises a conventional computer system and a handheld personal electronic device.

In some embodiments, an automated bioprocessing device further comprises a barcode reader, which is functionally connected to a control system of said automated bioprocessing device. Said barcode reader can scan a barcode and communicate operation parameters read from said barcode to said control system.

In some embodiments, an automated method of bioprocessing comprises: a) placing a biological sample inside a sample holder of a bioprocessing apparatus, said bioprocessing apparatus comprising i) a housing, ii) a cover, iii) one or more robot assemblies on said housing, each robot assembly configured to transport said sample holder and said biological samples therein from one said washing basin to another, and to agitate said biological samples within said washing basin;, and iv) a control system configured to operate said robot assembly according to a predetermined schedule, said control system comprising at least one bioprocessing controller; b) attaching said sample holder to said robot assembly of said bioprocessing apparatus; dispensing processing fluids to designated washing basins of said bioprocessing apparatus; c) inputting processing commands to said control system; said commands comprising one or more of the following: i) prompting a user to input new set of processing commands; ii) prompting said user to press a start button; iii) lowering said sample holder into a designated washing chamber; iv) agitating said sample holder in said designated washing chamber at a predetermined frequency for a predetermined time; v) raising said sample holder above the upper surface of said removable washing basin assembly; vi) transporting said sample holder to the next designated washing chamber; vii) prompting said user to remove said sample holder and biological samples therein; viii) moving said robot assembly back to its home position; d) initiating the bioprocessing according to said processing commands.

In some embodiments, an automated method of bioprocessing comprises a method for blotting. In some embodiments, an automated method of bioprocessing comprises a method for staining slides. In some embodiments, an automated method of bioprocessing comprises a method for isolation of nucleic acids.

These and other aspects and embodiments of the present invention will be appreciated from the following detailed description of the invention, along with the accompanying figures.

BRIEF DESCRIPTION OF THE DRAWINGS

The object and features of the present invention can be more fully understood and better appreciated with reference to the attached drawings, which are schematic representations only and not necessarily drawn to scale, wherein.

DETAILED DESCRIPTION ON THE INVENTION

Figure 1:
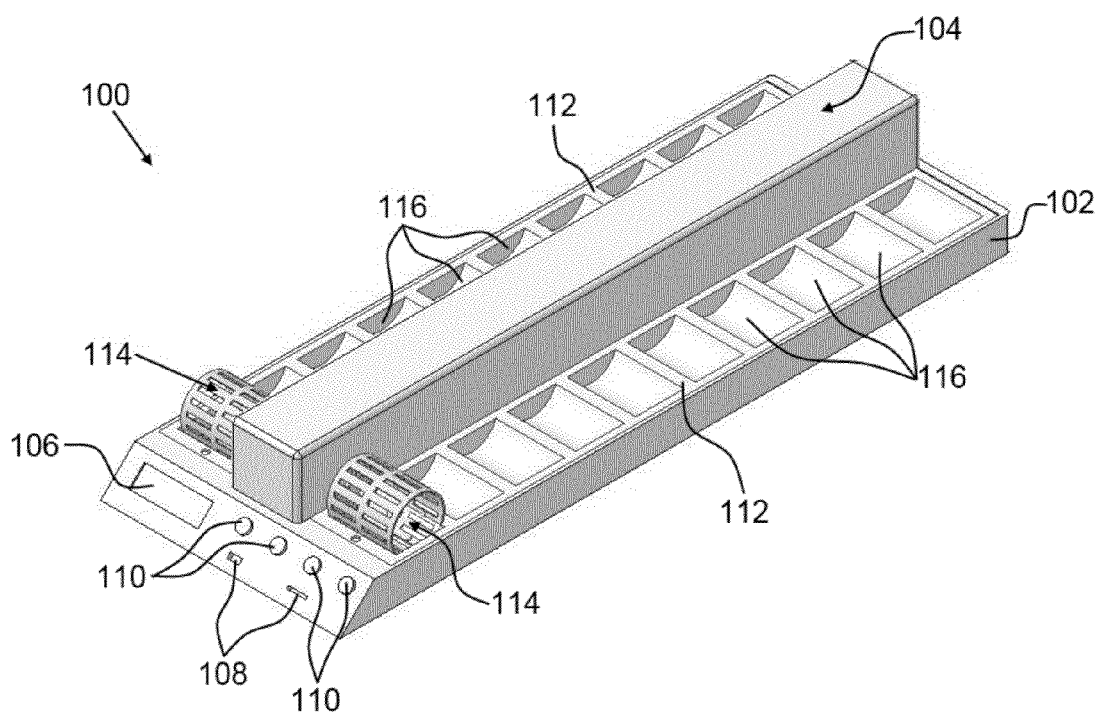
FIG. 1 shows an embodiment of an automated bioprocessing device 100 in accordance with the present invention.

The present invention relates to an improved apparatus and methods for processing biological samples using automation. The following description is presented to enable one of ordinary skill in the art to make and use the invention and is provided in the context of a patent application and its requirements. Various modifications to the preferred embodiment will be readily apparent to those skilled in the art and the generic principles herein may be applied to other embodiments and combination thereof. Although various components are discussed in the context of a particular initial design, it should be understood that the various elements can be altered and even replaced or omitted to permit other designs and functionality. Thus, the present invention is not intended to be limited to the embodiments shown but is to be accorded the widest scope consistent with the principles and features described herein. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

With a biomolecule is meant any of the organic molecules produced by living organisms; biomolecules consist primarily of carbon and hydrogen, nitrogen and oxygen, including proteins, peptides, polysaccharides, nucleic acids, amino acids, lipids, DNA and RNA. With a biological sample is meant a sample carrying any biomolecules either on a solid support or in a solution; the biological sample may be a clinical, biochemical, agricultural, environmental, laboratory, food, forensic sample or any other possible samples.

The term "connected" when used with reference to the relationship either between a rotation mechanism and a sample holder or between a translation mechanism and a sample holder is intended to include both the physical connection and the magnetic connection between the partners of the relationship.

A chaotropic agent, also known as chaotropic reagent and chaotrope, is a substance which disrupts the three dimensional structure in macromolecules such as proteins, DNA, or RNA and denatures them. Chaotropic agents interfere with stabilizing intramolecular interactions mediated by non-covalent forces such as hydrogen bonds, van der Waals forces, and hydrophobic effects. Known chaotropic agents include urea, thiourea, guanidinium chloride, guanidinium thiocyanate, and lithium perchlorate.

The automated bioprocessing devices and automated bioprocessing methods disclosed herein include automated devices and methods for performing one or more protocols for processing biomolecules. In some embodiments, the bioprocessing device may include performing assays on biological samples mounted on microscope slides. In some embodiments, the bioprocessing device may include the use of labeled molecules, wherein the labels include, for example, immunofluorescence or fluorescent labels. In some embodiments, the protocols for processing biomolecules are dealing with biomolecules that are immobilized on a solid support, such as a blotting membrane with bound biomolecules. As such, the protocols can be protocols for processing western blots (i.e., immunoblots), northern blots, or Southern blots. The automated bioprocessing devices and automated bioprocessing methods disclosed herein provide for automated bioprocessing that increase the efficiency and flexibility of persons operating such bioprocessing while providing performance that is at least as good as, if not better than similar manual processing.

To appreciate the features and advantages of preferred apparatuses and methods in accordance with the present invention, the reader is referred to the appended FIGS. 1-24 in conjunction with the following discussion. It is to be understood that the drawings are diagrammatic and schematic representations only and are neither limiting of the scope of the present invention nor necessarily drawn to scale.

I. Bioprocessing Devices

In a first aspect, a device is disclosed which provides for automated bioprocessing of biological samples. The bioprocessing device can take a variety of forms. The embodiments will be described below in conjunction with an automated device shown in FIG. 1. The principles of operation of the device are applicable to other types of automated bioprocessing devices according to the present invention.

FIG. 1 shows an embodiment of an automated bioprocessing device 100 in accordance with the present invention. The bioprocessing device 100 comprises a rectangular housing 102 surrounding a robot assembly 104, two removable washing basin assemblies 112, and a cover (not shown). It is to be understood that more removable washing basin assemblies can be added in parallel to the ones shown in FIG. 1. The housing 102 may be constructed from any suitable materials, such as metals, plastics, composite materials, or any combination thereof, and which is designed to house the various components of the device. The washing basin assembly 112 retains a plurality of washing basins 116 into which a sample holder 114 can be placed. In the embodiment shown, each washing basin assembly 112 may hold up to 10 washing basins 116, but the washing basin assembly 112 may be designed to hold any suitable number of washing basins 116. The depth of the washing basin 116 is preferably in the range from 1 to 5 cm, more preferably in the range from 2 to 4 cm. The length of the washing basin 116 is preferably in the range from 5 to 12 cm, more preferably in the range from 7 to 9 cm.

The width of the washing basin 116 is preferably in the range from 2 to 12 cm, more preferably in the range from 4 to 9 cm. The volume of each washing basin 116 might be the same as or different from other washing basins 116 in the same washing basin assembly 112. Different processing fluids can be placed in each washing basin 116 and be applied to a biological sample placed inside the sample holder 114. The robot assembly 104 can rotate the sample holder 114 within each washing basin 116 and move the sample holder 114 between different washing basins 116. The robot assembly 104 comprises at least one motor. The device 100 also includes a display screen 106, connectors 108, and a plurality of buttons 110.

Figure 2A:
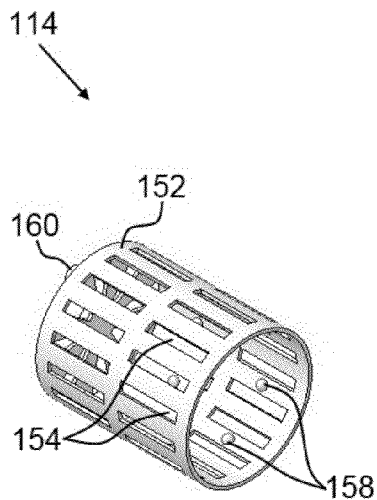
FIG. 2A is an illustration of a sample holder 114.
Figure 2B:
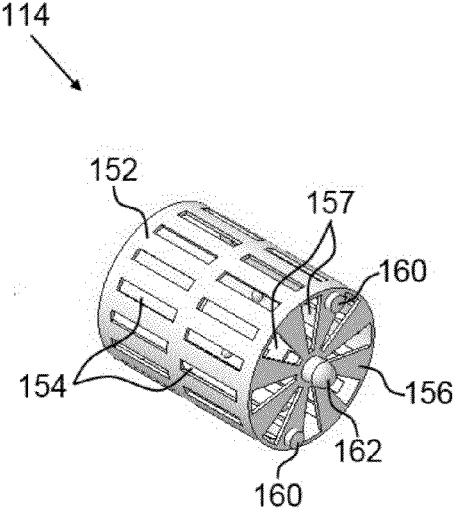
FIG. 2B is an illustration of a sample holder 114.

FIGS. 2A and 2B illustrate two views of the sample holder 114. The sample holder 114 comprises a cylinder body 152, on which there are a plurality of openings 154 to allow for free flow of processing fluids into and out of the sample holder 114. On the inside surface of cylinder body 152 there are a plurality of bumps 158, which are positioned to prevent the solid support of a biological sample from sticking tightly to the inside surface of cylinder body 152 and blocking the flow of liquid through the openings 154. On one end of the cylinder body 152 is a cap 156, on which there are a plurality of openings 157 to allow for free flow of processing fluids into and out the sample holder 114, two magnetic plates 160, and a protrusion 162 to prevent the sample holder 114 from staying outside the washing basin 116. The radius of the cylinder body 152 is preferably in the range from 1 to 10 cm, more preferably in the range from 2 to 5 cm. The length of the cylinder body 152 is preferably in the range from 4 to 11 cm, more preferably in the range from 7 to 9 cm. It is to be understood that when more than 2 removable washing basin assemblies are used in parallel, a sample holder used further away from the robot assembly 104 need to be modified and coupled to the movement of the sample holders closer to robot assembly 104, whereby both sample holders move in sync. For example, a cap on one sample holder may be connected to another cap on the second sample holder.

Figure 3:
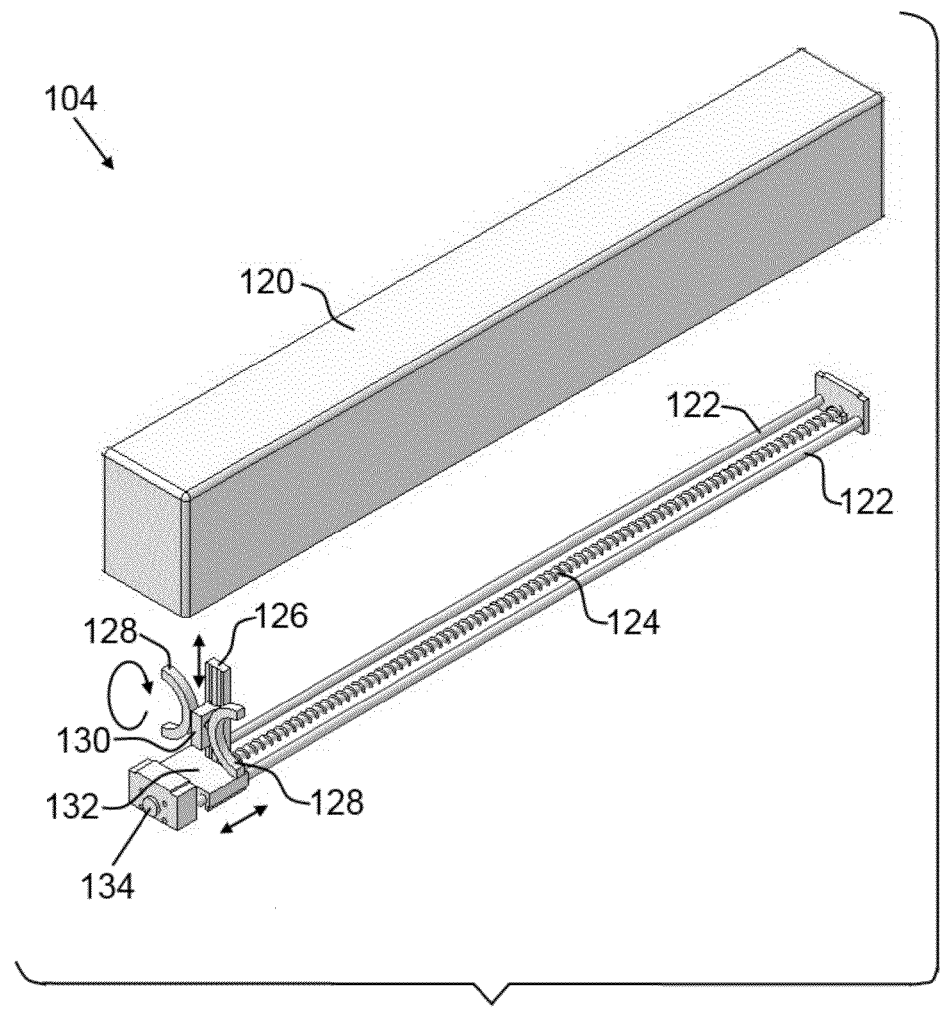
FIG. 3 shows an exploded view of an embodiment of the robot assembly 104.

FIG. 3 provides an exploded view of one embodiment of the robot assembly 104 depicted in FIG. 1. As shown in FIG. 3, the robot assembly 104 includes a protective cover 120, two guide rails 122, a screw shaft 124, a motor 134 to rotate the screw shaft 124, and a carriage 132 sitting on the screw shaft 124 and supported by guide rails 122. The protective cover 120 may be constructed from any suitable materials, such as plastics, that are generally transparent to magnetic forces, and may provide basic protection for the internal components, and may have an easy to clean surface. The screw shaft 124 powered by the motor 134 moves the carriage 132 along the horizontal direction. On the carriage 132 there is a translation mechanism 126 which moves both a rotation mechanism 130 and two permanent magnets 128 along the vertical direction in reference to the carriage 132. The permanent magnet 128 is controlled by the rotation mechanism 130.

In one embodiment, an operator may use buttons 110 in FIG. 1 to turn on and interact with the device 100, whose control system includes at least one bioprocessing controller (not shown) and might include one programmable control unit (not shown), to select various options and perform various functions. Said bioprocessing controller controls the robot assembly 104 to move the sample holder 114 from one washing basin to another, rotate the sample holder 114 at a predetermined speed and during a set period in each washing basin 116. Suitable programmable control unit comprises a conventional computer system and a handheld personal electronic device, such as an iPhone. Said computer system with an input/output card may connect with the bioprocessing device 100 via the connector 108, and run a computer program capable of controlling the operation of the robot assembly 104. Said handheld personal electronic device may download an appropriate program for the bioprocessing procedure from the internet and upload said program to the bioprocessing device 100 via the connector 108.

It is understood that said bioprocessing controller of device 100 controls the motor 134, the translation mechanism 126, and the rotation mechanism 130. The arrangement is such that when the motor 134 rotates the screw shaft 124 in forward and reverse direction, the carriage 132 is linearly reciprocated in the axial direction of the screw shaft 124 and is placed at a precise position along the axial direction of the screw shaft 124. At the start of the bioprocessing, the carriage 132 stays at the home position, at which the permanent magnets 128 attracts and holds the sample holder 114 together with a biological sample therein in the first washing basin 116, which is filled with the first processing fluid. The magnetic plates 160 on sample holder 114 allow the sample holder 114 to be attracted to and moved with the permanent magnet 128. Part or the entire biological sample placed in sample holder 114 is in contact with the first processing fluid. After the bioprocessing begins, the rotation mechanism 130 rotates the permanent magnet 128, which in turn rotates the sample holder 114 and the biological sample therein. A full rotation essentially washes the surface area of the biological sample with the first processing fluid. Constant rotation evenly disperses the first processing fluid over the surface of the biological sample. After reaching the set time for the treatment in the first washing basin 116, the rotation mechanism 130 stops rotating and the translation mechanism 126 raises the sample holder 114 and the biological sample therein via the magnetic force exerted by the magnet 128, which is being raised together with the rotation mechanism 130 on the carriage 132. Once the sample holder is raised out of the first washing basin 116, the translation mechanism 126 stops moving and holds the sample holder above the top surface of the washing basin assembly 112. Then the motor 134 moves the carriage 132, together with the sample holder 114, to the position for the second washing basin 116 which is filled with the second processing fluid. The translation mechanism 126 lowers the sample holder 114 into the second washing basin 116 and the rotation mechanism 130 resumes rotating the sample holder 114 together with the biological sample inside. This sequence of rotating and moving repeats itself until the sample holder 114 finishes rotating in the last washing basin 116. At that time after removal of the sample holder 114 and the biological sample inside, the carriage 132 moves back to the home position. The removable washing basin assembly 112 is removed and disposed.

Figure 4:
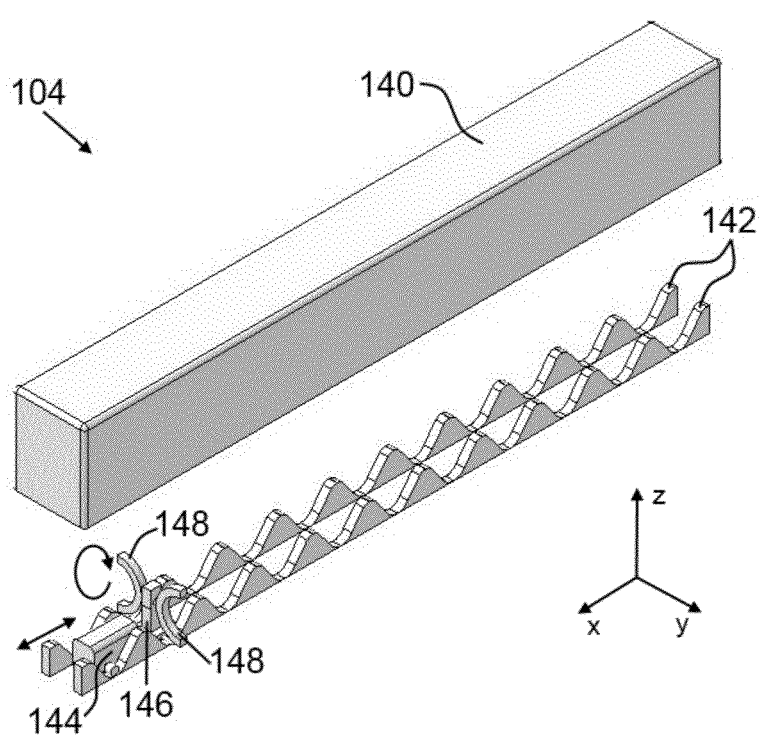
FIG. 4 shows an exploded view of an embodiment of the robot assembly 104.

FIG. 4 provides an exploded view of another embodiment of the robot assembly 104 depicted in FIG. 1. As shown in FIG. 4, the robot assembly 104 includes a protective cover 140, two guiding tracks 142, and a cart 144 which is powered by a motor (not shown) and has four wheels standing on the guiding tracks 142. On the cart 144 is a rotation mechanism 146 which controls and rotates two permanent magnets 148. The protective cover 140 may be constructed from any suitable materials, such as plastics, that are generally transparent to magnetic forces, and may provide basic protection for the internal components, and may have an easy to clean surface. The guiding tracks 142 provide a path for the cart 144 to move vertically along the Z-axis in FIG. 4 when the cart 144 moves horizontally along the X-axis in FIG. 4. In addition, the spacing of the troughs on the guiding tracks 142 is the same as the spacing of washing basins 116 in the removable washing basin assembly 112. The depth of the troughs on the guiding tracks 142 is longer than the depth of the washing basin 116, wherein the difference between said depths is preferably in the range from 1 to 10 cm, more preferably in the range from 1 to 3 cm.

In one embodiment, the arrangement is such that when the cart 144 stays at the home position, the permanent magnet 148 attracts and holds sample holder 114 together with a biological sample therein in the first washing basin 116, which is filled with the first processing fluid. After the bioprocessing begins, the rotation mechanism 146 rotates the permanent magnet 148, which in turn rotates the sample holder 114 and the biological sample therein. A full rotation essentially washes the surface area of the biological sample with the first processing fluid. Constant rotation evenly disperses the first processing fluid over the surface of the biological sample. After reaching the set time for the treatment in the first washing basin 116, the rotation mechanism 146 stops rotating and the cart 144 starts to move on the guiding track 142 along the X-axis. Due to the curved nature of guiding track 142, the cart 144 also moves along the Z-axis while moving along the X-axis. The arrangement is such that the sample holder 114, which is still attracted to and held by the permanent magnet 148, moves with the cart 144 from the first washing basin 116 to the second washing basin 116. After the sample holder 114 reaches the second washing basin 116, the cart 144 stops; and the rotation mechanism 146 resumes rotating the sample holder 114 together with the biological sample inside. This sequence of rotating and moving repeats itself until the sample holder 114 finishes rotating in the last washing basin 116. At that time after removal of the sample holder 114 and the biological sample inside, the cart 144 moves back to the home position. The removable washing basin assembly 112 is removed and disposed.

Figure 5:
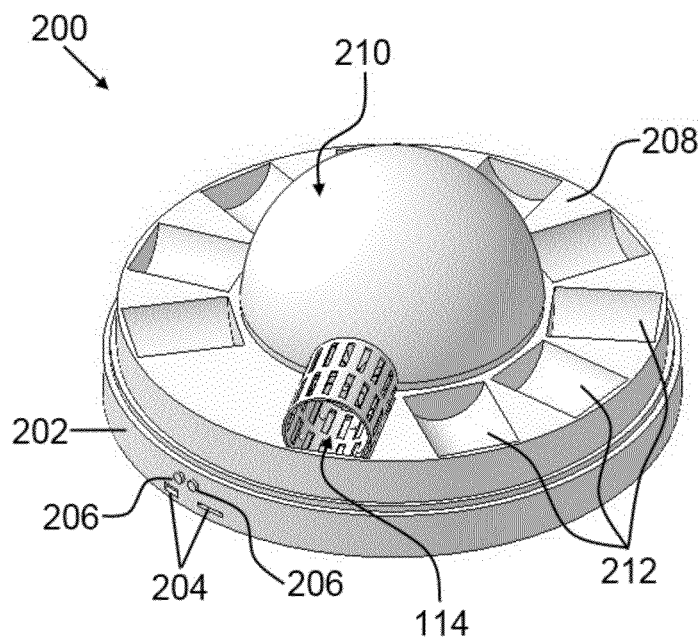
FIG. 5 shows an embodiment of an automated bioprocessing device 200 in accordance with the present invention.

FIG. 5 shows a preferred embodiment of an automated bioprocessing device 200 in accordance with the present invention. The bioprocessing device 200 comprises a circular housing 202 surrounding a robot assembly 210, a removable washing basin assembly 208, and a cover (not shown). The housing 202 may be constructed from any suitable materials, such as metals, plastics, composite materials, or any combination thereof, and which is designed to house the various components of the device. The washing basin assembly 208 retains a plurality of washing basins 212 into which a sample holder 114 can be placed. In the embodiment shown, each washing basin assembly 208 may hold up to 10 washing basins 212, but the washing basin assembly 208 may be designed to hold any suitable number of washing basins 212. The depth of the washing basin 212 is preferably in the range from 1 to 5 cm, more preferably in the range from 2 to 4 cm. The length of the washing basin 212 is preferably in the range from 5 to 12 cm, more preferably in the range from 7 to 9 cm. The width of the washing basin 212 is preferably in the range from 2 to 12 cm, more preferably in the range from 4 to 9 cm. Different processing fluids can be placed in each washing basin 212 and be applied to a biological sample placed inside the sample holder 114. The robot assembly 210 can rotate the sample holder 114 within each washing basin 212 and move the sample holder 114 between different washing basins 212. The robot assembly 210 comprises at least one motor. As shown in FIG. 5, the device 200 also includes connectors 204, and a plurality of buttons 206.

Figure 6:
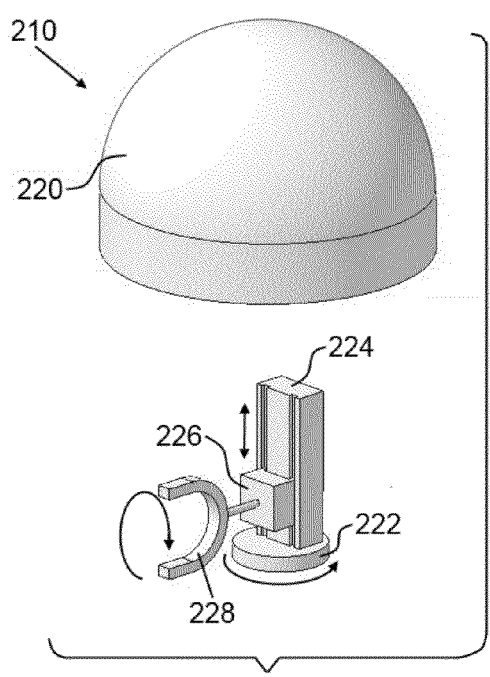
FIG. 6 shows an exploded view of an embodiment of robot assembly 210.

FIG. 6 provides an exploded view of one embodiment of the robot assembly 210 depicted in FIG. 5. As shown in FIG. 6, the robot assembly 210 includes a protective cover 220 and a rotation mechanism 222, on which stands a translation mechanism 224 together with a rotation mechanism 226 and a permanent magnet 228. The protective cover 220 may be constructed from any suitable materials, such as plastics, that are generally transparent to magnetic forces, and may provide basic protection for the internal components, and may have an easy to clean surface. The rotation mechanism 222 rotates the translation mechanism 224 and the rotation mechanism 226 around the central, vertical axis in reference to washing basin assembly 208. The translation mechanism 224 moves both the rotation mechanism 226 and the permanent magnets 228 along the vertical direction. The permanent magnet 228 is attached to and controlled by the rotation mechanism 226.

In one embodiment, an operator may use buttons 206 in FIG. 5 to turn on and interact with the device 200, whose control system includes at least one bioprocessing controller (not shown) and might include one programmable control unit (not shown), to select various options and to perform various functions. Said bioprocessing controller controls the robot assembly 210 to move the sample holder 114 from one washing basin to another, and rotate the sample holder 114 at a predetermined speed and during a set period in each washing basin 212. Suitable programmable control unit comprises a conventional computer system and a handheld personal electronic device, such as an iPhone. Said computer system with an input/output card may connect with the bioprocessing device 200 via the connector 204, and run a computer program capable of controlling the operation of the robot assembly 210. Said handheld personal electronic device may download an appropriate program for the bioprocessing procedure from the internet and upload the said program to the bioprocessing device 200 via the connector 204.

It is understood that said bioprocessing controller of device 200 controls the rotation mechanism 222, the translation mechanism 224, and the rotation mechanism 226. The arrangement is such that the translation mechanism 224 and the rotation mechanism 226 can be placed at a precise position during the bioprocessing sequence. At the start of the bioprocessing, the rotation mechanism 222 stays at the home position, at which the permanent magnets 228 attracts and holds the sample holder 114, together with a biological sample, in the first washing basin 212, which is filled with the first processing fluid. The magnetic plates 160 on sample holder 114 allow the sample holder 114 to be attracted to and moved with the permanent magnet 228. Part of the biological sample placed in sample holder 114 is in contact with the first processing fluid. After the bioprocessing begins, the rotation mechanism 226 rotates the permanent magnet 228, which in turn rotates the sample holder 114 and the biological sample inside the sample holder 114. A full rotation essentially washes the surface area of the biological sample with the first processing fluid. Constant rotation evenly disperses the first processing fluid over the surface of the biological sample. After reaching the set time for the treatment in the first washing basin 212 the rotation mechanism 226 stops rotating. The translation mechanism 224 raises the sample holder 114 and the biological sample via the magnetic force exerted by the magnet 228, which is being raised together with the rotation mechanism 226. Once the sample holder 114 is raised out of the first washing basin 212, the translation mechanism 224 stops moving and holds the sample holder 114 above the surface of the washing basin assembly 208. The rotation mechanism 222 moves translation mechanism 224, together with the sample holder 114, at a position above the second washing basin 212, which is filled with the second processing fluid. The translation mechanism 224 lowers the sample holder 114 into the second washing basin 212 and the rotation mechanism 226 resumes rotating the sample holder 114 together with the biological sample inside. This sequence of rotating and moving the sample holder 114 repeats itself until the sample holder 114 finishes rotating in the last washing basin 212. At that time after removal of the sample holder 114 and the biological sample inside, the rotation mechanism 222 moves back to the home position. The removable washing basin assembly 208 is removed and disposed.

Figure 7:
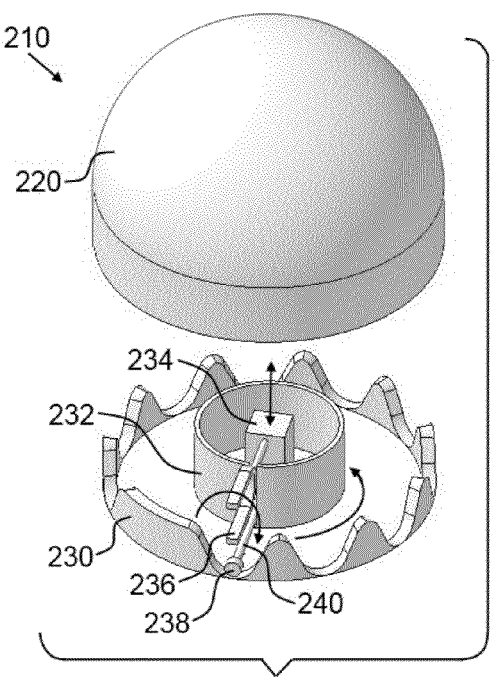
FIG. 7 shows an exploded view of an embodiment of the robot assembly 210.

FIG. 7 provides an exploded view of another embodiment of the robot assembly 210 depicted in FIG. 5. As shown in FIG. 7, the robot assembly 210 includes a protective cover 220, a guiding track 230, a rotation mechanism 232 in the shape of an open cylinder with an opening on the sidewall, and a cart 234. The cart 234 locates at the center of the rotation mechanism 232 and it may reciprocate along the central, vertical axis around which the rotation mechanism 232 rotates. The cart 234 also has a rotatable permanent magnet 236, which is controlled and powered by the cart 234. In addition, the cart 234 has a shaft 240 to which a wheel 238 is connected. The wheel 238 stands on the guiding track 230. The permanent magnet 236 and the shaft 240 extend out of the rotation mechanism 232 through the said opening thereon. When the rotation mechanism 232 rotates, the edge of said opening pushes the shaft 240 in the same direction of the rotation and forces the wheel 238 to move on the guiding track 230. As a result, the wheel 238 on the guiding track 230 provides a mechanism for the cart 234 to slide vertically while rotating around said central, vertical axis when the rotation mechanism 232 rotates. In addition, the spacing of the troughs on the guiding track 232 is the same as the spacing of washing basins 212 in the removable washing basin assembly 208. The depth of the troughs on the guiding track 232 is longer than the depth of the washing basin 212, wherein the difference between said depths is preferably in a range from 1 to 10 cm, more preferably in a range from 1 to 3 cm.

In one embodiment, the arrangement is such that when the cart 234 stays at the home position, the permanent magnet 236 attracts and holds sample holder 114 together with a biological sample in the first washing basin 212, which is filled with the first processing fluid. After the bioprocessing begins, the cart 234 rotates the permanent magnet 236, which in turn rotates the sample holder 114 and the biological sample therein. A full rotation essentially washes the surface area of the biological sample with the first processing fluid. Constant rotation evenly disperses the first processing fluid over the surface of the biological sample. After reaching the set time for the treatment in the first washing basin 212, the cart 234 stops rotating the permanent magnet 236 and the rotation mechanism 232 rotates around said central, vertical axis. The edge of said opening on the rotation mechanism 232 pushes the magnet 236, the shaft 240, the wheel 238, and the cart 234 to rotate in the same direction. When the wheel 238 moves on the guiding track 230, due to the curved nature of the guiding track 230, the cart 234 also slides vertically while rotating. The arrangement is such that the sample holder 114, which is still attracted to and held by the permanent magnet 236, moves with the cart 234 from the first washing basin 212 to the second washing basin 212. After the sample holder 114 reaches the second washing basin 212, the rotation mechanism 232 stops and the cart 234 resumes rotating the sample holder 114. This sequence of rotation and transportation of the sample holder 114 repeats itself until the sample holder finishes rotating in the last washing basin 212. At that time after removal of the sample holder 114 and the biological sample inside, the cart 234 moves back to the home position. The removable washing basin assembly 208 is removed and disposed.

Figure 8:
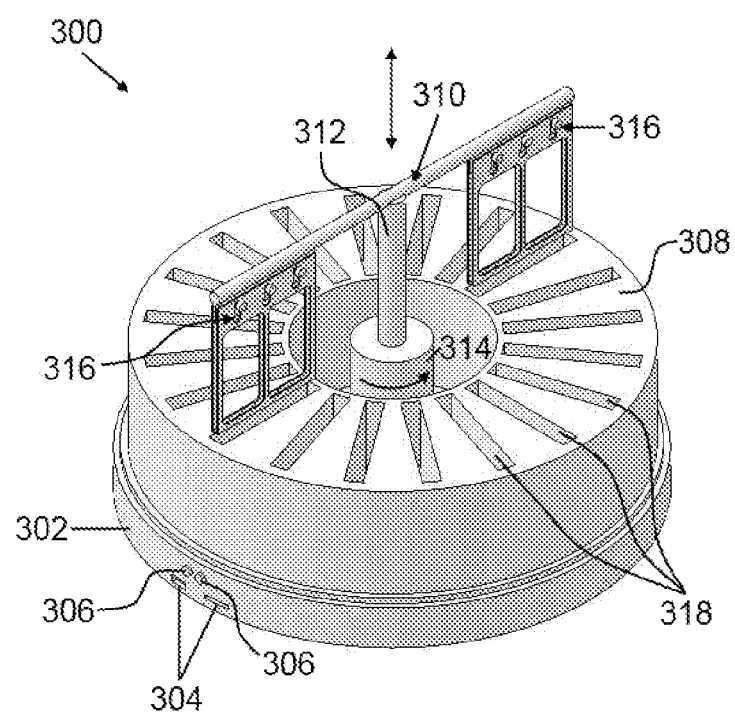
FIG. 8 shows an embodiment of an automated bioprocessing device 300 in accordance with the present invention.

FIG. 8 shows a preferred embodiment of an automated bioprocessing device 300 in accordance with the present invention. The bioprocessing device 300 comprises a circular housing 302, on which stand a removable washing basin assembly 308 and a robot assembly comprising a rotation mechanism 314 and a translation mechanism 312, and a cover (not shown). The bioprocessing device 300 further comprises a sample holding arm 310 which is connected to and controlled by the translation mechanism 312, and two sample holders 316. The washing basin assembly 308 retains a plurality of washing basins 318 into which the sample holder 316 can be placed. In the embodiment shown, each washing basin assembly 308 may hold up to 20 washing basins 318, but the washing basin assembly 308 may be designed to hold any suitable number of washing basins 318, each of which may be the same as or different from other washing basins. The depth of the washing basin 318 is preferably in the range from 1 to 12 cm, more preferably in the range from 5 to 10 cm. The length of the washing basin 318 is preferably in the range from 5 to 12 cm, more preferably in the range from 7 to 10 cm. The width of the washing basin 318 is preferably in the range from 1 to 6 cm, more preferably in the range from 2 to 4 cm. Different processing fluids can be placed in each washing basin 318 and be applied to a biological sample placed inside the sample holder 316. The translation mechanism 312 might reciprocate sample holder 316 within each washing basin 318 along the central, vertical direction in reference to the top surface of the washing assembly 308. The rotation mechanism 314 might rotate the translation mechanism 312 and the sample holders 316 on the horizontal plane parallel with the top surface of the washing assembly 308. The combined action of the translation mechanism 312 and the rotation mechanism 314 might move the sample holder 316 between different washing basins 318. The device 300 also includes connectors 304 and a plurality of buttons 306.

Figure 9:
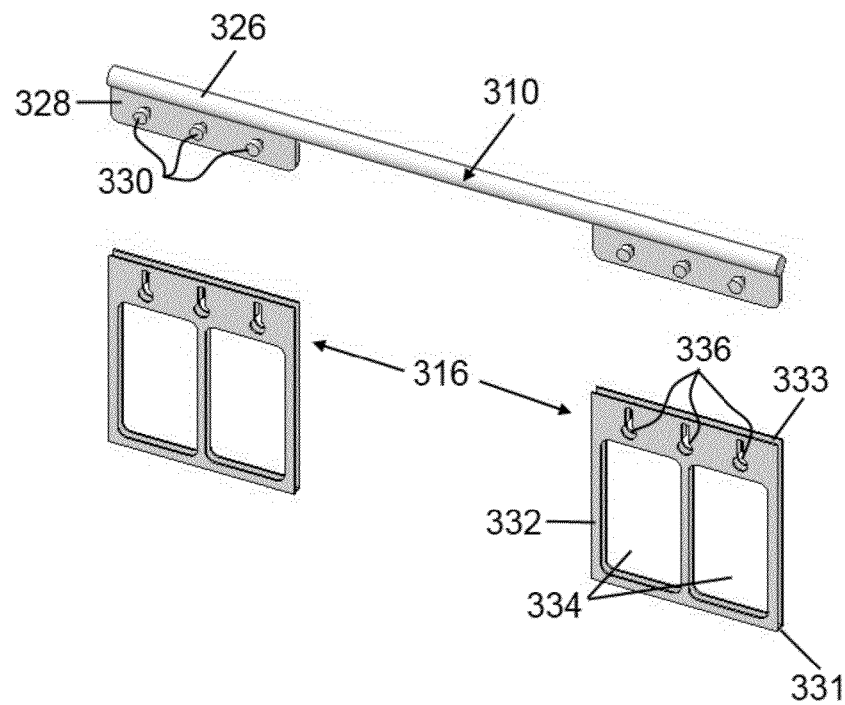
FIG. 9 is a detail view of a sample holding arm 310 and two sample holders 316.

FIG. 9 provides a detail view of the sample holding arm 310 and two sample holders 316 depicted in FIG. 8. As shown in FIG. 9, the sample holding arm 310 includes a holding shaft 326, on each end of which there is a flat holding plate 328. On both faces of the holding plate 328 are a plurality of holding knobs 330. The sample holder 316 might be used to hold a blot membrane. As shown in FIG. 9, the sample holder 316 may be folded along the fold 331 to form two portions of the sample holder 316, portion 332 and portion 333, between which a blot membrane may be placed. Both portions 332 and 333 have fluid flow openings 334 to allow for the free flow of process fluids around both sides of the membrane. In addition, both portions 332 and 333 have a plurality of perforations 336 to hang the sample holder 316 onto the holding buttons 330 on the holding plate 328. The sample holder 316 may be constructed from any suitable materials including plastics, such as PVC, HDPE, polyesters, and APET, and may be injection molded or be assembled from injection molded pieces or may be die cut.

In one embodiment, an operator may use buttons 306 in FIG. 8 to turn on and interact with the device 300, whose control system includes at least one bioprocessing controller (not shown) and might include one programmable control unit (not shown), to select various options and perform various functions. Said bioprocessing controller controls the translation mechanism 312 to move the sample holder 316 along the vertical direction within the washing basin 318, control the rotation mechanism 314 to rotate the sample holder 316 from above one washing basin to above the next washing basin, and set the timing and speed of each movement of the sample holder 316. Suitable programmable control unit comprises a conventional computer system and a handheld personal electronic device, such as an iPhone. Said computer system with an input/output card may connect with the bioprocessing device 300 via the connector 304, and run a computer program capable of controlling the operation of the device 300. Said handheld personal electronic device may download an appropriate program for the bioprocessing procedure from the internet and upload the said program to the bioprocessing device 300 via the connector 304.

It is understood that under the control of the said bioprocessing controller, the arrangement is such that the sample holder 316 can be placed at a precise position during the bioprocessing sequence. At the start of the bioprocessing, the rotation mechanism 314 stays at the home position, at which the sample holder 316 holds a biological sample above the first washing basin 318, which is filled with the first processing fluid. After the bioprocessing begins, the translation mechanism 312 lowers the sample holder 316 into the first washing basin 318 until all the membrane is in contact with the first processing fluid. The translation mechanism 312 reciprocates the sample holder 316 within the first washing basin 318 at a set speed and for a set time, resulting in mixing the first processing fluid which washes both sides of the membrane effectively. After reaching the set time for the treatment in the first washing basin 318, the translation mechanism 312 raises the sample holder 316 and the biological sample out of the first washing basin 318. The rotation mechanism 314 rotates translation mechanism 312 so that the sample holder 316 is at a position above the second washing basin 318, which is filled with the second processing fluid. The translation mechanism 312 lowers the sample holder 316 into the second washing basin 318 and restarts the reciprocation. This sequence of reciprocation and transportation repeats itself until the sample holder 316 finishes the treatment in the last washing basin 318. At that time after removal of the sample holders 316 and the biological samples therein, the rotation mechanism 314 moves back to the home position. The removable washing basin assembly 308 is removed and disposed.

Figure 10:
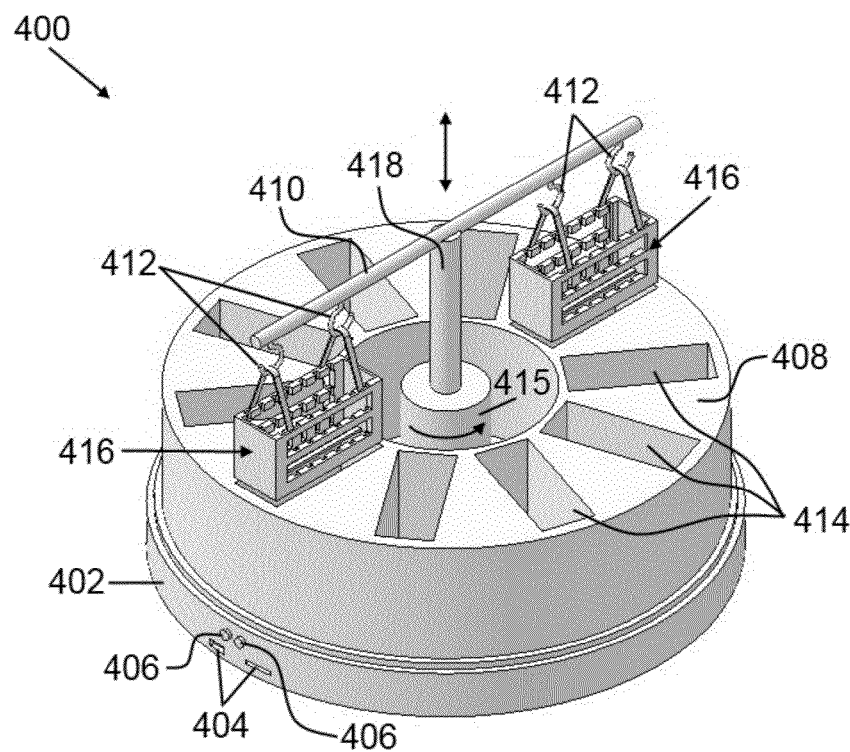
FIG. 10 shows an embodiment of an automated bioprocessing device 400 in accordance with the present invention.

FIG. 10 shows a preferred embodiment of an automated bioprocessing device 400 in accordance with the present invention. The bioprocessing device 400 comprises a circular housing 402, on which stand a removable washing basin assembly 408 and a robot assembly comprising a rotation mechanism 415 and a translation mechanism 418, and a cover (not shown). The bioprocessing device further comprises a sample holding arm 410, which is connected to and controlled by the translation mechanism 418, and two sample holders 416. On each end of the sample holding arm 410 are two hooks 412. The washing basin assembly 408 retains a plurality of washing basins 414 into which the sample holder 416 can be placed. In the embodiment shown, each washing basin assembly 408 may hold up to 10 washing basins 414, but the washing basin assembly 408 may be designed to hold any suitable number of washing basins 414, each of which may be the same as or different from other washing basins. The depth of the washing basin 414 is preferably in the range from 1 to 12 cm, more preferably in the range from 4 to 10 cm. The length of the washing basin 318 is preferably in the range from 5 to 12 cm, more preferably in the range from 7 to 10 cm. The width of the washing basin 318 is preferably in the range from 1 to 8 cm, more preferably in the range from 2 to 6 cm. Different processing fluids can be placed in each washing basin 414 and be applied to biological samples placed inside the sample holder 416. The translation mechanism 418 might reciprocate sample holder 416 within each washing basin 414 along the vertical direction. The rotation mechanism 415 might rotate the translation mechanism 418 and the sample holders 416 on the horizontal plane parallel with the top surface of the washing assembly 408. The combined action of the translation mechanism 418 and the rotation mechanism 415 might move the sample holder 416 between different washing basins 414. The device 400 also includes connectors 404, and a plurality of buttons 406.

Figure 11:
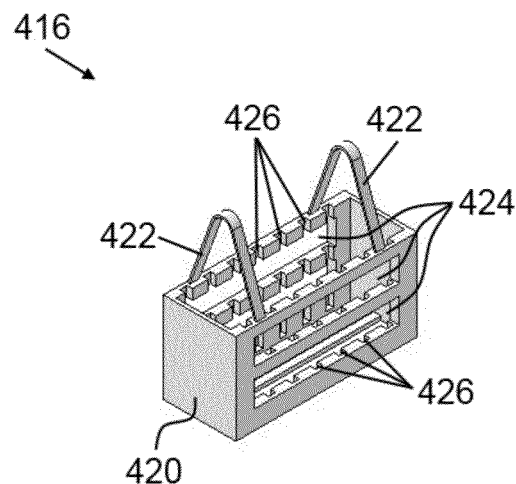
FIG. 11 provides a detail view of a sample holder 416.

FIG. 11 provides a detail view of the sample holder 416 depicted in FIG. 10. As shown in FIG. 11, the sample holder 416 includes a frame 420 and two stripes 422 attached thereto. Stripes 422 might be used to hang the sample holder 416 onto the hooks 412. There are a plurality of fluid flow openings 424 on the sides and the bottom of the frame 420 to allow for the free flow of process fluids in-between slides inserted in the frame 420. In addition, there are a plurality of slots 426 of a predetermined width on two opposing sides of frame 420 to allow for the insertion of biological samples such as staining slides.

In one embodiment, an operator may use buttons 406 in FIG. 10 to turn on and interact with the device 400, whose control system includes at least one bioprocessing controller (not shown) and might include one programmable control unit (not shown), to select various options and perform various functions. Said bioprocessing controller controls the translation mechanism 418 to move the sample holder 416 along the vertical direction within the washing basin 414, control the rotation mechanism 415 to rotate the sample holder 416 around the central vertical axis from above one washing basin to above the next washing basin, and set the timing and speed of each movement of the sample holder 416. Suitable programmable control unit comprises a conventional computer system and a handheld personal electronic device, such as an iPhone. Said computer system with an input/output card may connect with the bioprocessing device 400 via the connector 404, and run a computer program capable of controlling the operation of the device 400. Said handheld personal electronic device may download an appropriate program for the bioprocessing procedure from the internet and upload the said program to the bioprocessing device 400 via the connector 404.

It is understood that under the control of the said bioprocessing controller, the arrangement is such that the sample holder 416 can be placed at a precise position during the bioprocessing sequence. At the start of the bioprocessing, the rotation mechanism 415 stays at the home position, at which the sample holder 416 holds at least one biological sample, such as a staining slide, above the first washing basin 414, which is filled with the first processing fluid. After the bioprocessing begins, the translation mechanism 418 lowers the sample holder 416 into the first washing basin until all the surfaces of said biological sample are in contact with the first processing fluid. The translation mechanism 415 reciprocates the sample holder 416 along the vertical direction within the first washing basin at a set speed and for a set time, resulting in mixing and agitating the first processing fluid which washes the surfaces of said biological sample. After reaching the set time for the treatment in the first washing basin, the translation mechanism 418 raises the sample holder 416 and said biological sample out of the first washing basin 414. The rotation mechanism 415 rotates translation mechanism 418 so that the sample holder 416 is at a position above the second washing basin 414, which is filled with the second processing fluid. The translation mechanism 418 lowers the sample holder 416 into the second washing basin 414 and restarts the reciprocation. This sequence of reciprocation and transportation of sample holder 416 repeats itself until the sample holder 416 finishes the treatment in the last washing basin 414. At that time after removal of the sample holders 416 and the biological samples therein, the rotation mechanism 415 moves back to the home position. The removable washing basin assembly 308 is removed and disposed.

Figure 12:
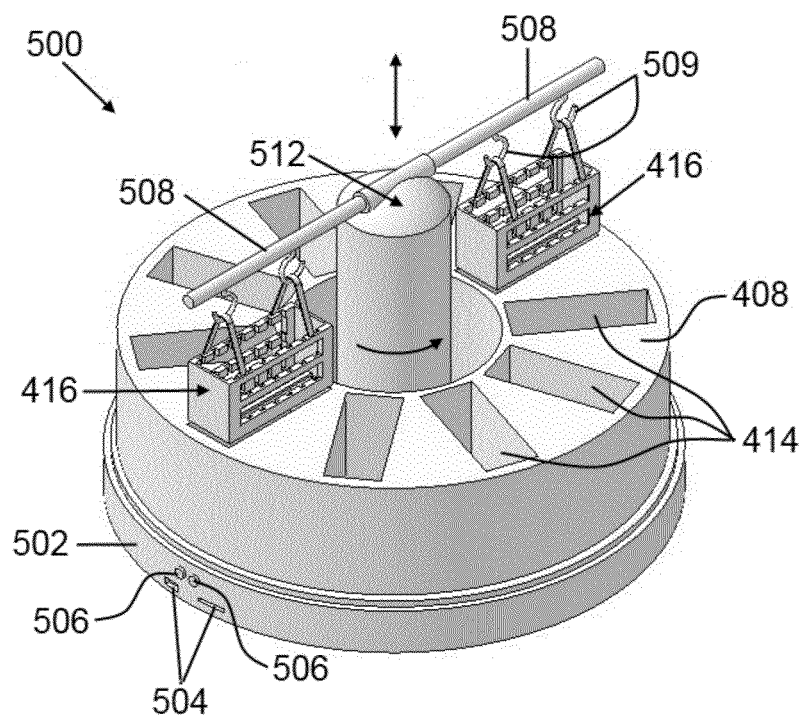
FIG. 12 shows an embodiment of an automated bioprocessing device 500 in accordance with the present invention.

FIG. 12 shows a preferred embodiment of an automated bioprocessing device 500 in accordance with the present invention. The bioprocessing device 500 comprises a circular housing 502, on which stand a removable washing basin assembly 408 and a robot assembly 512, and a cover (not shown). The bioprocessing device 500 further comprises two sample holding arms 508, which are attached to and controlled by the robot assembly 512. On each side of the sample holding arm 508 there are two hooks 509, which might hold a sample holder 416. The robot assembly 512 might reciprocate the sample holder 416 within each washing basin 414 along the vertical direction and move the sample holder 416 from one washing basin 414 to the next washing basin 414. As shown in FIG. 12, the device 500 also includes connectors 504, and a plurality of buttons 506.

Figure 13:
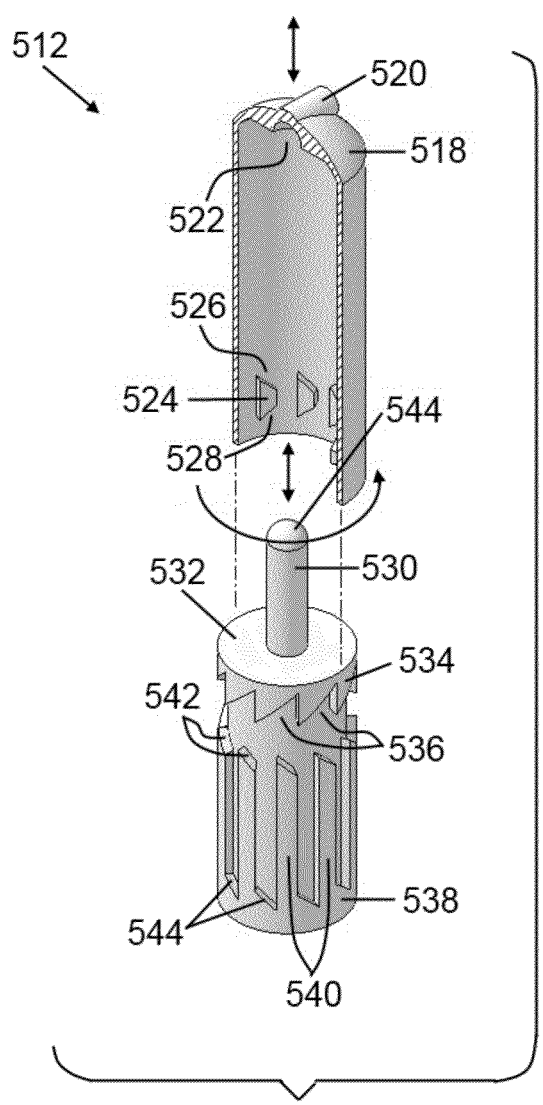
FIG. 13 provides partially cut perspective view of a robot assembly 512

FIG. 13 provides an exploded, partially cut perspective view of the robot assembly 512 depicted in FIG. 12. As shown in FIG. 13, the robot assembly 512 comprises a rotational shell 518, a translation mechanism 530 and a stationary cylinder 532. The stationary cylinder 532, which is fixedly mounted on the housing 502, has a hole in the longitudinal direction at the center, through which the translation mechanism 530 can move freely in the longitudinal direction. The top of the translation mechanism 530 is a hemisphere 544 of a predetermined radius. An inclined protruding stopper 538 of a predetermined thickness is formed along the outer wall near the bottom of the stationary cylinder 532 while a sawtooth stopper 534 of a predetermined thickness is formed along the outer wall near the top of the stationary cylinder 532.

The rotational shell 518 includes two locks 520 for each of the two sample holding arms 508 at the top of the outer walls of the rotational shell 518. At the top center of the inner wall of the rotational shell 518 is a concavity 522, the shape of which matches that of the hemisphere 538 of the translation mechanism 530 and allows the rotational shell 518 to sit on top of the translation mechanism 530 in such a way that the rotational shell 518 can both rotate around the longitudinal direction when forced, and move along said longitudinal direction when the translation mechanism 530 moves in the same direction.

A plurality of shell-rotation side protrusions 524 are formed at the lower portion of the inner wall of the rotational shell 518. In one embodiment of the present invention, 10 shell-rotation side protrusions 524 are mounted along the inner walls and spaced 36 degree apart. Each of the protrusions 524 protrudes to a predetermined thickness from the wall of the shell 518. An upper inclined surface 526 of each shell-rotation side protrusions 524 is manufactured to have the same angle as each tooth of the sawtooth stopper 534. A lower inclined surface 528 of each shell-rotation side protrusions 524 is made to have the same angle as each of the inclined surfaces 542 and 544 of the inclined protruding stopper 538.

In one embodiment, an operator may use buttons 506 in FIG. 12 to turn on and interact with the device 500, whose control system includes at least one bioprocessing controller (not shown) and might include one programmable control unit (not shown), to select various options and perform various functions. Said bioprocessing controller controls the movement of the robot assembly 512, either moving along the vertical direction within the washing basin 414 or moving between different washing basins 414.

Referring to FIGS. 12 and 13, in an assembled state when the translation mechanism 530 is at its lowest position, each shell-rotation side protrusion 524 is engaged with one lower inclined surface 544 and at least one side protruding bar 540. As a result, the shell-rotation side protrusions 524 come to a standstill and so do the robot assembly 512 and the sample holders 416. Consequently the sample holders 416 and biological samples therein are kept at their lowest positions in the washing basin 414.

When the translation mechanism 530 moves upward along the longitudinal direction, the hemisphere 544 pushes the concavity 522 and the rotational shell 518 along the same direction. Since the adjacent side protruding bars 540 restrict the lateral movement of each shell-rotation side protrusion 524, the shell-rotation side protrusions 524, as well as the rotational shell 518, move substantially on a straight line along the edges of the side protruding bars 540. This restricted movement corresponds to moving the sample holder 416 along the vertical direction within the washing basin 414.

When the shell-rotation side protrusions 524 touch the inclined surfaces 536 of the sawtooth stopper 534, the shell-rotation side protrusions 524 glide along the inclined surfaces 536. As a result, the rotational shell 518 is rotated at a predetermined angle in the direction of an arrow shown in FIG. 13 until the shell-rotation side protrusions 524 are stopped by the sawtooth stopper 534 to cause a standstill for the rotational shell 518. This first rotation corresponds to partially moving the sample holder 416 from one washing basin 414 to the next washing basin 414 above the top surface of the removable washing basin assembly 408.

When the translation mechanism 530 moves downward, the rotational shell 518 moves downward as well. When the shell-rotation side protrusions 524 touch the upper inclined surfaces 542, the shell-rotation side protrusions 524 glide along the upper inclined surfaces 542, and as a result, the rotational cylinder 518 is rotated at a predetermined angle in the direction of an arrow shown in FIG. 13. This second rotation completes the moving of the sample holder 416 from one washing basin 414 to the next washing basin 414 above the top surface of the removable washing basin assembly 408. Further downward, longitudinal movement of the translation mechanism 530 together with the rotational shell 518 along a substantially straight line lowers the sample holder 416 to the next washing basin 414, ready for another round of treatment of the biological samples with the next processing fluid.

Figure 14:
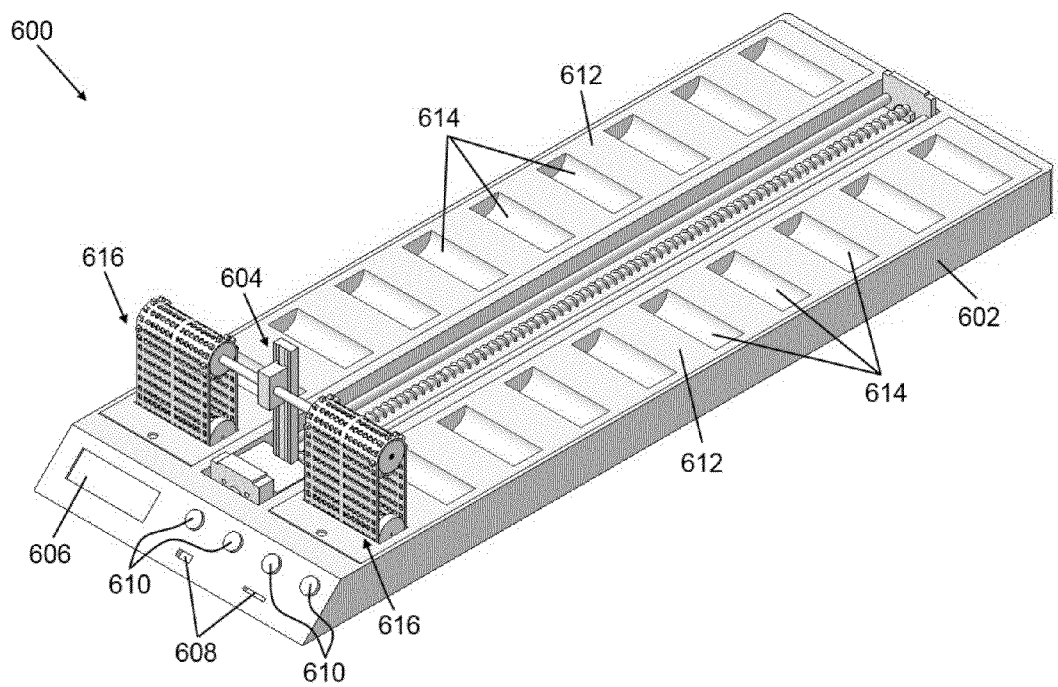
FIG. 14 depicts an embodiment of an automated bioprocessing device 600 in accordance with the present invention.

FIG. 14 shows an embodiment of an automated bioprocessing device 600 in accordance with the present invention. The bioprocessing device 600 comprises a rectangular housing 602 surrounding a robot assembly 604, two removable washing basin assemblies 612, and a cover (not shown). The washing basin assembly 612 retains a plurality of washing basins 614 into which a sample holder 616 can be placed. In the embodiment shown, each washing basin assembly 612 may hold up to 10 washing basins 614, but the washing basin assembly 612 may be designed to hold any suitable number of washing basins 614. The depth of the washing basin 614 is preferably in the range from 1 to 5 cm, more preferably in the range from 1 to 4 cm. The length of the washing basin 614 is preferably in the range from 5 to 12 cm, more preferably in the range from 7 to 9 cm. The width of the washing basin 614 is preferably in the range from 1 to 6 cm, more preferably in the range from 2 to 4 cm. The volume of each washing basin 614 might be the same as or different from other washing basins 614. Different processing fluids can be placed in each washing basin 614 and be applied to a biological sample placed inside the sample holder 616. The robot assembly 604 can rotate the sample holder 616 within each washing basin 614 and move the sample holder 616 between different washing basins 614. The robot assembly 604 comprises at least one motor. The device 600 also includes a display screen 606, connectors 608, and a plurality of buttons 610.

Figure 15:
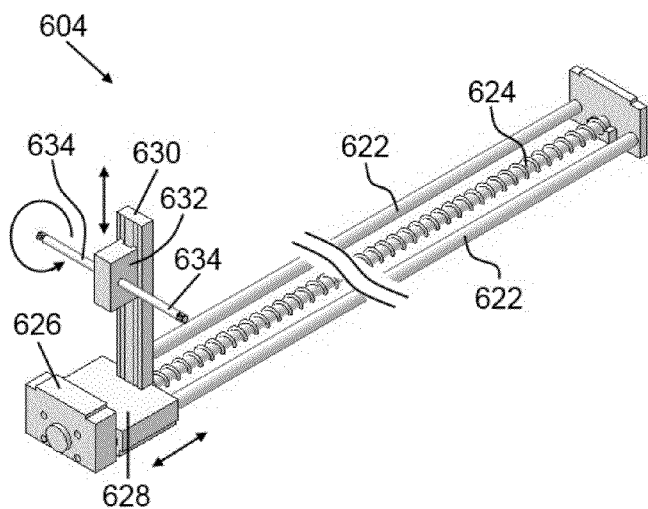
FIG. 15 shows a detailed view of the robot assembly 604.

FIG. 15 provides a detailed view of the robot assembly 604 depicted in FIG. 14. As shown in FIG. 15, the robot assembly 604 includes two guide rails 622, a screw shaft 624, a motor 626 to rotate the screw shaft 624, and a carriage 628 sitting on the screw shaft 624 and supported by guide rails 622. The screw shaft 624 powered by the motor 626 moves the carriage 628 along a horizontal direction. On the carriage 628 there is a translation mechanism 630 which moves a rotation mechanism 632 and two shafts 634 along a vertical direction. The shaft 634 is controlled by the rotation mechanism 632.

Figure 16:
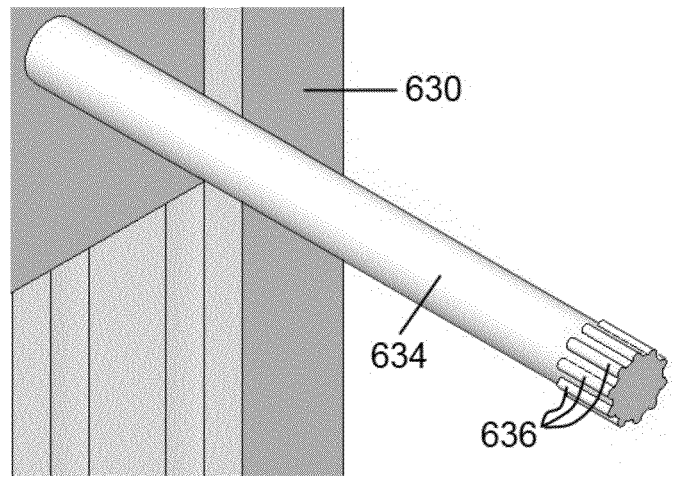
FIG. 16 affords an enlarged view of part of the rotation shaft 634.

FIG. 16 affords an expanded view of part of the rotation shaft 634. As shown in FIG. 16, there are a plurality of protrusions 636 spaced concentrically at one end of the rotation shaft 634.

Figure 17:
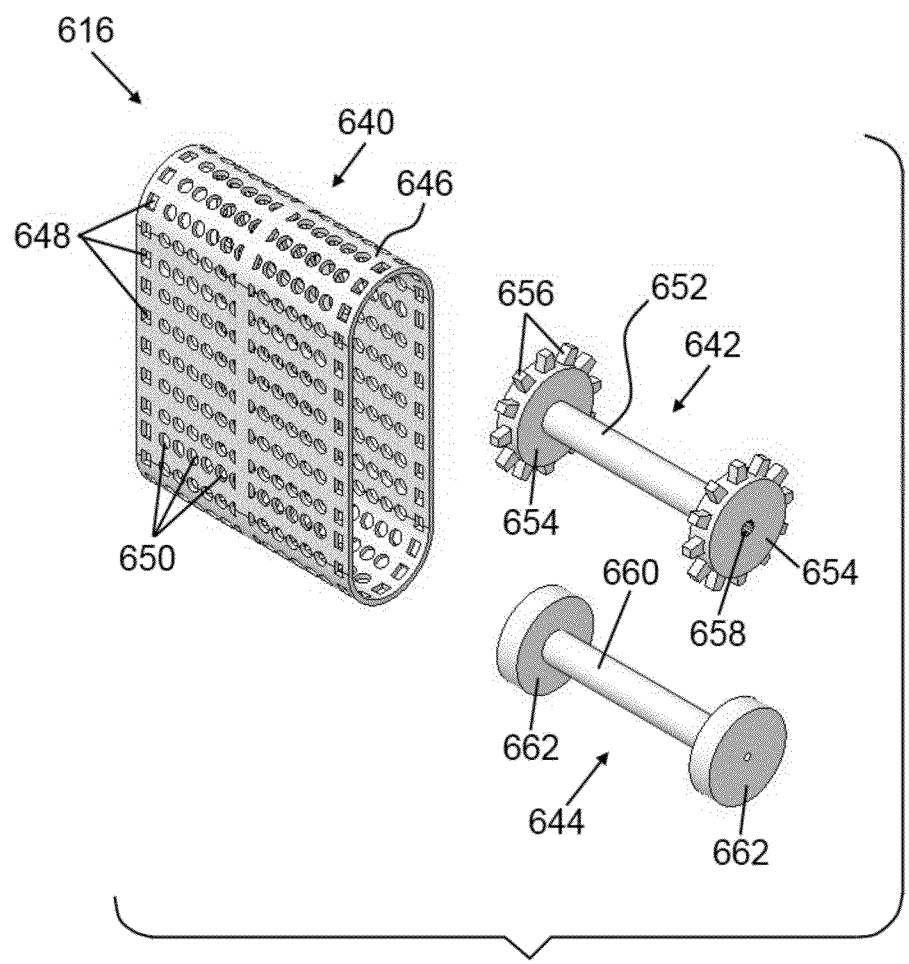
FIG. 17 shows an exploded, detailed view of the sample holder 616.
Figure 18:
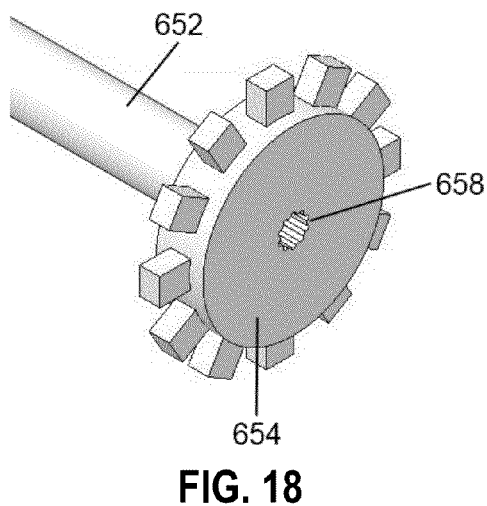
FIG. 18 provides an enlarged view of part of the of the rotation reel 642.

FIG. 17 provides an exploded, detailed view of the sample holder 616 depicted in FIG. 14. As shown in FIG. 17, the sample holder 616 includes a continuous flexible sheet 640, a rotation reel 642, and a dead weight 644. The continuous flexible sheet 640 may be constructed from any suitable materials, such as metals, plastics, composite materials, or any combination thereof, which are designed to be bendable under sufficient outside forces. The continuous flexible sheet 640 comprises a sheet body 646, on which there are a plurality of openings 650 to allow for the free flow of processing fluids into and out of the sample holder 616. The continuous flexible sheet 640 also has a set of regularly-spaced perforations 648 near each rim of the continuous flexible sheet 640. Optionally there are a plurality of bumps on the inside surface of the continuous flexible sheet 640. The dead weight 644 comprises two wheels 662 connected by a shaft 660. The rotation reel 642 comprises two sprockets 654 and a shaft 652 connecting sprockets 654. On each sprockets 654 are a plurality of gear teeth 656, which are configured to engage the continuous flexible sheet 640 if inserted into the perforations 648 thereon. As shown in FIG. 18, at the center of the sprocket 654 there is a cavity 658, whose shape is complimentary to that of the end of the rotation shaft 634 bearing protrusions 636. The configuration is such that said end of the rotation shaft 634 bearing protrusions 636 can be pushed into the cavity 658 of the rotation reel 642, and, as a result, a rotating shaft 634 can engage the rotation reel 642 and the continuous flexible sheet 640 so that they all rotate in sync.

In one embodiment, an operator may use buttons 610 in FIG. 14 to turn on and interact with the device 600, whose control system includes at least one bioprocessing controller (not shown) and might include one programmable control unit (not shown), to select various options and perform various functions. Said bioprocessing controller controls the robot assembly 604 to move the sample holder 616 from one washing basin to another, rotate the sample holder 616 at a predetermined speed and during a set period in each washing basin 614. Suitable programmable control unit comprises a conventional computer system and a handheld personal electronic device, such as an iPhone. Said computer system with an input/output card may connect with the bioprocessing device 600 via the connector 608, and run a computer program capable of controlling the operation of the robot assembly 604. Said handheld personal electronic device may download an appropriate program for the bioprocessing procedure from the internet and upload said program to the bioprocessing device 600 via the connector 608.

It is understood that said bioprocessing controller of device 600 controls the motor 626, the translation mechanism 630, and the rotation mechanism 632. The arrangement is such that when the motor 626 rotates the screw shaft 624 in forward and reverse direction, the carriage 628 is linearly reciprocated in the axial direction of the screw shaft 624 and is placed at a precise position along the axial direction of the screw shaft 624. At the start of the bioprocessing, the carriage 628 stays at the home position, at which the shaft 634 together with the rotation reel 642 attached thereto is above the first washing basin 614, which is filled with the first processing fluid. A biological sample is inserted inside a continuous flexible sheet 640, which is then hanged on the rotation reel 642 through the engagement of teeth 656 and perforations 648. A dead weight 644 is placed inside the bottom of the continuous flexible sheet 640. Care is taken to make sure the biological sample is between the space created by sheet body 646 and the shafts 652, 660.

After the bioprocessing begins, the translation mechanism lowers the bottom of the sample holder 616 into the first washing basin 614. The dead weight 644 is partially or wholly submerged into the first processing fluid, which causes part of the biological sample to be in contact with the first processing fluid. Subsequently the rotation mechanism 632 rotates the rotation shaft 634, which in turn rotates the rotation reel 642, whose gear teeth 656 engaged with perforations 648 force the flexible sheet 640 and the biological sample to rotate around the rotation reel 642. A full rotation of the flexible sheet 640 essentially washes the surface area of the biological sample with the first processing fluid. Constant rotation evenly disperses the first processing fluid over the surface of the biological sample. After reaching the set time for the treatment in the first washing basin 614, the rotation mechanism 632 stops rotating and the translation mechanism 630 raises the sample holder 616 and the biological sample therein as well as the rotation mechanism 632. Once the sample holder is raised out of the first washing basin 614, the translation mechanism 630 stops moving and holds the sample holder 616 above the top surface of the washing basin assembly 612. Then the motor 626 moves the carriage 628, together with the sample holder 616, to the position for the second washing basin 614 which is filled with the second processing fluid. The translation mechanism 630 lowers the bottom of the sample holder 616 into the second washing basin 614 and the rotation mechanism 632 resumes rotating the flexible sheet 640 together with the biological sample inside. This sequence of rotation and transportation repeats itself until the sample holder 616 finishes rotating in the last washing basin 614. At that time after removal of the sample holder 616 and the biological sample inside, the carriage 628 moves back to the home position. The removable washing basin assembly 612 is removed and disposed.

Figure 19:
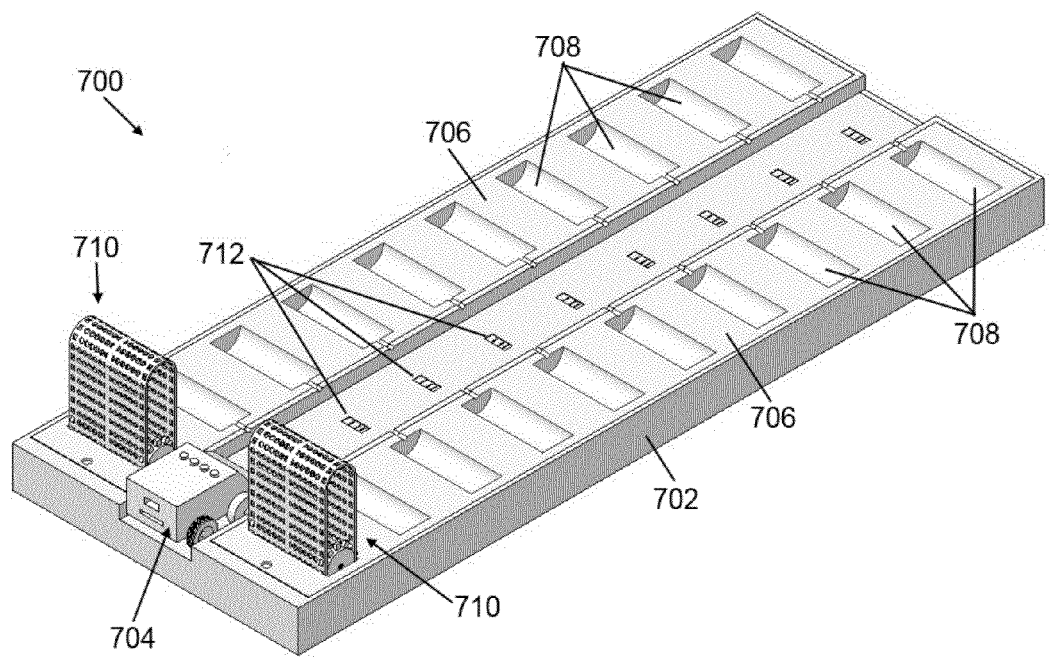
FIG. 19 depicts an embodiment of an automated bioprocessing device 700 in accordance with the present invention.

FIG. 19 shows an embodiment of an automated bioprocessing device 700 in accordance with the present invention. The bioprocessing device 700 comprises a rectangular housing 702, a robot assembly 704 on said housing, two removable washing basin assemblies 706, and a cover (not shown). The washing basin assembly 706 retains a plurality of washing basins 708 into which a sample holder 710 can be placed. In the embodiment shown, each washing basin assembly 706 may hold up to 10 washing basins 708, but the washing basin assembly 706 may be designed to hold any suitable number of washing basins 708. The depth of the washing basin 708 is preferably in the range from 1 to 5 cm, more preferably in the range from 1 to 4 cm. The length of the washing basin 708 is preferably in the range from 5 to 12 cm, more preferably in the range from 7 to 9 cm. The width of the washing basin 708 is preferably in the range from 1 to 6 cm, more preferably in the range from 2 to 4 cm. The volume of each washing basin 708 might be the same as or different from other washing basins 708. Different processing fluids can be placed in each washing basin 708 and be applied to a biological sample placed inside the sample holder 710. The robot assembly 704 can rotate the sample holder 710 within each washing basin 708 and move the sample holder 710 between different washing basins 708. The robot assembly 704 comprises at least one motor. There are also a plurality of barcodes 712 on the surface of housing 702, right on the path of the robot assembly 704.

Figure 20:
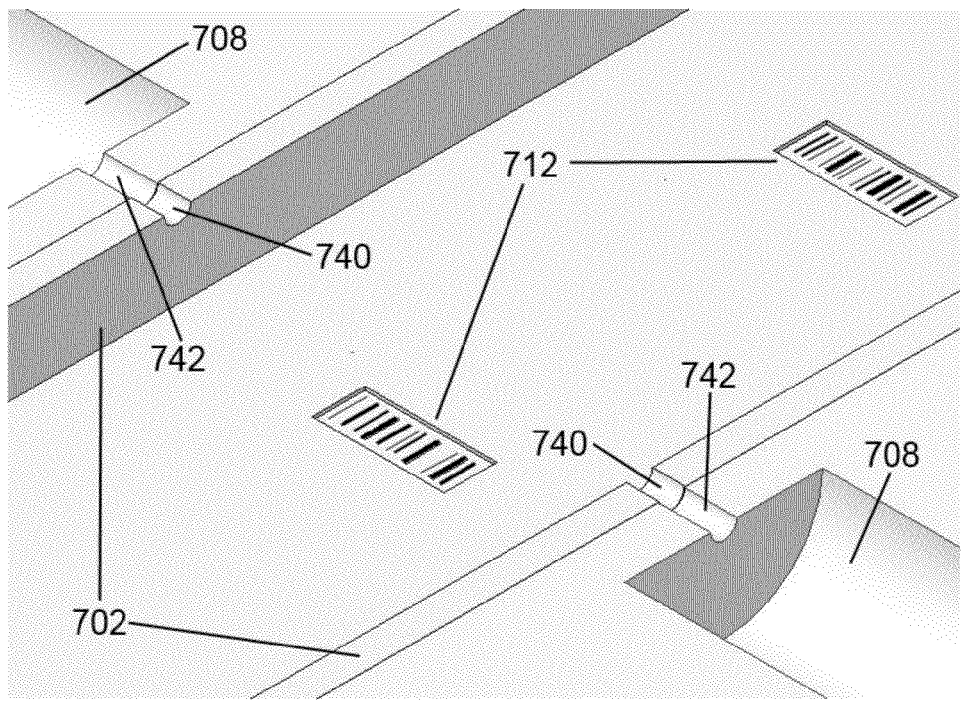
FIG. 20 shows an enlarged view of part of the bioprocessing device 700.

FIG. 20 provides an enlarged view of a part of the device 700. As shown in FIGS. 19 and 20, there are a plurality of indentures 742 on the washing basin assemble 706. There are also a plurality of matching indentures 740 on the housing 702. Together, the positions and alignment of indentures 740 and 742 allow smooth rotation of the rotation shaft 634 at each washing basin 708.

Figure 21:
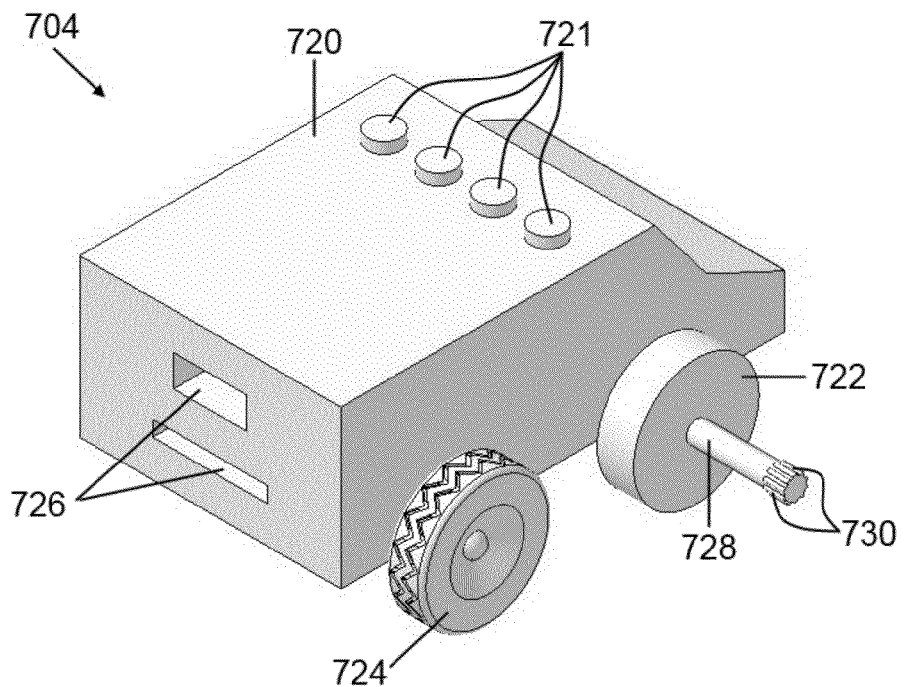
FIG. 21 provides a detailed view of the robot assembly 704.

FIG. 21 provides an enlarged view of the robot assembly 704 depicted in FIG. 19. The robot assembly 704 includes a robot body 720, two driving wheels 724 (one shown), and two rotation wheels 722 (one shown). Each rotation wheel 722 has a rotation shaft 728 at the center and each rotation shaft 728 has a plurality of protrusions 730 spaced concentrically at one end thereof. In addition, there are a plurality of buttons 721 on the top of the robot body 720, and connectors 726, which can be used to charge the robot assembly 704 and receive bioprocessing methods from a programmable control unit. The robot assembly 704 also comprises a first motor to power the driving wheels 724, a second motor to rotate the rotation wheels 722 and the rotation shaft 728, a bioprocessing controller to control said first and second motors, a barcode scanner in communication of said bioprocessing controller and capable of reading barcodes 712, and a battery to power said motors, said bioprocessing controller, and said barcode reader. The configuration is such that during operation, the rotation wheel 722 does not touch the surface of the moving path for the robot assembly 704. Hence, the rotation of the rotation wheel 722 does not move the robot assembly 704 forward or backward.

Figure 22:
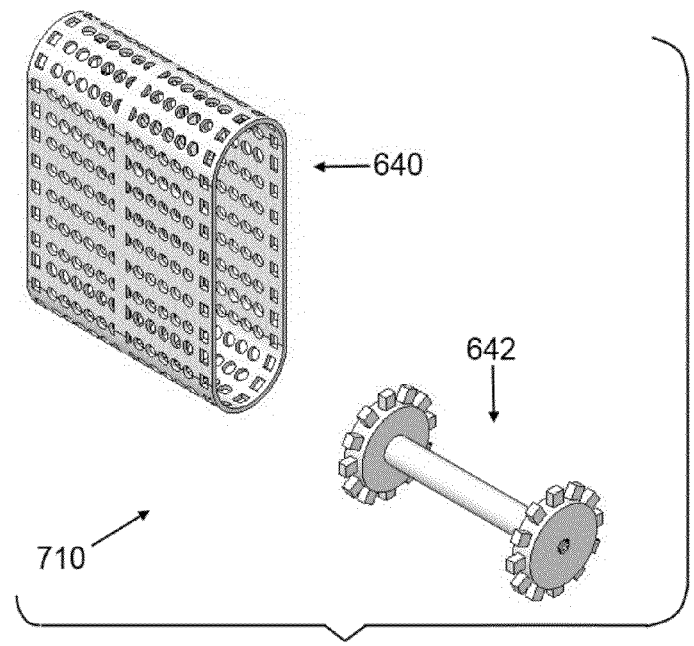
FIG. 22 depicts an exploded, detailed view of the sample holder 710.

FIG. 22 provides an exploded, detailed view of the sample holder 710 depicted in FIG. 19. As shown in FIG. 22, the sample holder 710 includes a flexible sheet 640 and a rotation reel 642, both of which have been described in FIGS. 17 and 18. The continuous flexible sheet 640 may be constructed from plastics materials, such as polyester and cellulose acetate, which have a combination of rigidity and flexibility to be used as a supporting material for the sample holder 710. The configuration is such that the end of the shaft 728 bearing protrusions 730 can be pushed into the cavity 658 of the rotation reel 642, and, as a result, a rotating shaft 728 can engage the rotation reel 642 and the continuous flexible sheet 640 to rotate in sync.

In one embodiment, an operator may use buttons 721 in FIG. 21 to turn on and interact with the device 700, whose control system includes at least one bioprocessing controller inside the robot assembly 704 to select various options and perform various functions. Said bioprocessing controller controls the robot assembly 704 to move the sample holder 710 from one washing basin 708 to another washing basin 708, and rotate the sample holder 710 at a predetermined speed and during a set period in each washing basin 708. In addition, said control system might include a suitable programmable control unit, which comprises a conventional computer system and a handheld personal electronic device, such as an iPhone. Said computer system with an input/output card may connect with the bioprocessing device 700 via the connector 726, and run a computer program capable of controlling the operation of the robot assembly 704. Said handheld personal electronic device may download an appropriate program for the bioprocessing procedure from the internet and upload said program to the bioprocessing device 700 via the connector 726.

In another embodiment, the barcode scanner at the bottom of the robot assembly 704 can scan the barcode at each processing position and transmit the operation parameters, such as the duration and speed of the rotation at each processing position, to the bioprocessing controller inside the robot assembly 704. When the robot assembly finishes bioprocessing at one position, it will move to the next position, scan the next barcode, and execute the operation until it reaches the final position.

It is understood that said bioprocessing controller of device 700 controls said first motor that powers the driving wheels 724. The arrangement is such that the robot assembly 704 can be placed at a precise position along the horizontal direction in-between two washing basin assemblies 706. At the start of the bioprocessing, the robot assembly 704 stays at the home position, at which the rotation shaft 728 together with the rotation reel 642 attached thereto is above the first washing basin 708, which is filled with the first processing fluid. A biological sample is inserted inside a continuous flexible sheet 640, which is then attached to the rotation reel 642 through the engagement of teeth 656 and perforations 648 at the bottom of the continuous flexible sheet 640. Care is taken to keep the biological sample between the continuous flexible sheet 640 and the shaft 652. Due to the rigidity of the continuous flexible sheet 640, the sample holder 710 remains in a substantially upright configuration.

After the bioprocessing begins, the bottom of the sample holder 710 is lowered into the first washing basin 708 and the rotation reel 642 is partially submerged into the first processing fluid. This causes part of the biological sample to be in contact with the first processing. Subsequently the rotation wheel 722 rotates the rotation shaft 728, which in turn rotates the rotation reel 642, whose gear teeth 656 engaged with perforations 648 force the continuous flexible sheet 640 and the biological sample to rotate around the rotation reel 642. A full rotation of the flexible sheet 640 essentially washes the surface area of the biological sample with the first processing fluid. Constant rotation evenly disperses the first processing fluid over the surface of the biological sample. After reaching the set time for the treatment in the first washing basin 708, the rotation wheel 722 stops rotating and said first motor powers the driving wheels 724 to move the robot assembly 704, together with the sample holder 710, to the position for the second washing basin 708 which is filled with the second processing fluid. Once the bottom of the sample holder 710 sinks into the second washing basin and the rotation shaft 728 rests in the indentures 740 and 742, the rotation wheel 722 resumes rotating the continuous flexible sheet 640 together with the biological sample inside. This sequence of rotation and transportation repeats itself until the sample holder 710 finishes rotating in the last washing basin 708. At that time after removal of the sample holder 710 and the biological sample inside, the robot assembly 704 is put back to the home position. The removable washing basin assembly 706 is removed and disposed.

Figure 23:
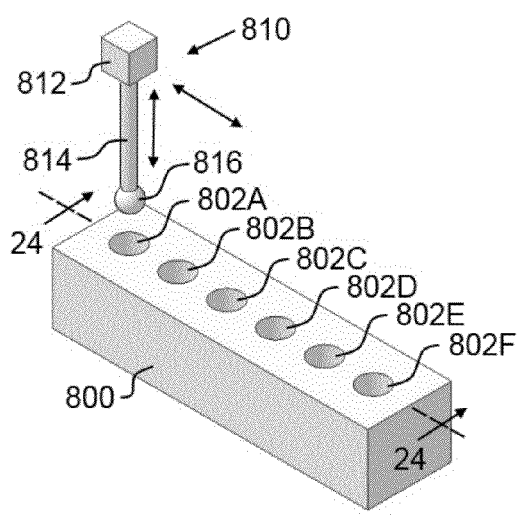
FIG. 23 shows sample holder 810 and removable washing basin assemble 800.

FIG. 23 shows an embodiment of a sample holder 810 and a washing basin assembly 800 in accordance with the present invention to be used in the isolation of nucleic acid. The sample holder 810 comprises a connection assembly 812, a sponge ball 816, and a shaft 814 which connects the connection assembly 812 and the sponge ball 816. The connection assembly 812 is connected to and controlled by a robot assembly (not shown) in such a way that the sample holder 810 can be moved in both the vertical and the horizontal directions shown in FIG. 23. The sponge ball 816 comprises a silica membrane in the middle section, with the silica membrane parallel to the horizontal direction and sandwiched by sponges. The washing basin assembly 800 retains a plurality of washing basins from 802A to 802F, into which a sample holder 810 can be placed. In the embodiment shown, each washing basin assembly 800 may hold up to 6 washing basins, but the washing basin assembly 800 may be designed to hold any suitable number of washing basins.

Figure 24:
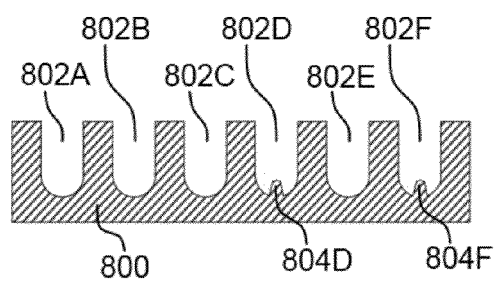
FIG. 24 is a sectional view of removable washing basin assembly 800.

FIG. 24 provides a sectional view of washing basin assemble 800. As shown in FIG. 24, washing basins 802D, 802F comprise respectively a bump 804D, 804F at the bottom of each washing basin.

Before the start of the nucleic acid isolation process, nucleic acid samples to be purified is either absorbed onto said silica membrane of the sponge ball 816 or placed in high chaotropic salt binding buffer in washing basin 802A; high chaotropic salt washing buffer is also placed in washing basin 802B; 70% ethanol solution is placed in washing basin 802C; and water is placed in washing basin 802E. Once the process starts, the robot assembly reciprocates the sponge ball 816 in each washing basin on washing basin assembly 800 and moves the sponge ball 816 from one washing basin to another on the washing basin assembly 800. In washing basin 802A, if crude nucleic acid is present in the processing fluid, said nucleic acid is absorbed to the silica membrane inside the sponge ball 816. In washing basin 802B, impurities including proteins are washed away from the silica membrane inside the sponge ball 816. In washing basin 802C, salts are washed away from the silica membrane inside the sponge ball 816. In washing basin 802D, when the sponge ball 816 is pressed on the bump 804D at the bottom, solutions absorbed by the sponge is forced to drain out. In washing basin 802E, the sponge ball 816 absorbs water, which washes off the nucleic acid from the silica membrane into the water. In washing basin 802F, when the sponge ball 816 is pressed on the bump 804F at the bottom, solutions containing nucleic acid which is absorbed by the sponge is forced to drain out and collected by the operator. After that, the removable washing basin assembly 800 and the sample holder 810 are removed and disposed.

It is understood that many parameters for the aforementioned processing of a biological sample can be defined and modified by a user.

II. Methods of Bioprocessing

In some embodiments, methods of bioprocessing include: providing a sample holder, where the sample holder contains at least one biological sample; attaching the sample holder to a robot assembly of a bioprocessing apparatus; where the bioprocessing apparatus comprises a housing, a cover, a washing basin assembly, a sample holder, at least one robot assembly, and a control system; dispensing processing fluids into designated washing basins of said bioprocessing apparatus; inputting processing commands to said control system, said commands comprising one or more of the following: i) prompting a user to press a start button; ii) lowering said sample holder into a designated washing chamber; iii) agitating said sample holder in said designated washing chamber at a predetermined frequency for a predetermined time; iv) raising said sample holder above the upper surface of said removable washing basin assembly; v) transporting said sample holder to the next designated washing chamber; vi) prompting said user to remove said sample holder and biological samples therein; vii) moving said sample holder to its home position; and viii) prompting said user to input new set of processing commands; initiating the bioprocessing according to said processing commands; and removing said biological sample.

In some embodiments, processing fluids, including blocking buffers and washing buffers, may be pre-loaded into designated washing basins to save time for the researcher who is running the bioprocessing. The researcher only needs to add antibody solutions to the designated washing basins before starting the blotting program.

In some embodiments, the process fluids dispensed may be any suitable solvent, solution or reagent for use in the desired bioprocess, including but not limited to liquid reagents used for chemical reactions, solvents or solutions used for washing, antibody solutions, buffer solutions, blocking buffer solutions and solutions containing fluorescent labeling reagents. The process fluids also may include samples that are to be processed such as proteins, nucleic acids and other biomolecules, cells, cell lysates, and combinations thereof. In some embodiments, the at least one processing fluid includes at least one blocking buffer. In some embodiments, the at least one processing fluid includes at least one antibody. In some embodiments, the at least one processing fluid includes at least one washing fluid. In some embodiments, the salt solution concentration may be any suitable concentration for improving yield, for example, a concentration of between about 0.1 M and about 6 M.

In some embodiments, agitating a sample holder includes rotating the sample holder containing said biological sample for a set time within a washing basin which contains a processing fluid. In some embodiments, agitating a sample holder includes reciprocating the sample holder containing said biological sample along the vertical direction for a set time within a washing basin which contains a processing fluid.

In some embodiments, agitating a sample holder includes agitating a filter or filter membrane in a sample holder in at least one processing fluid. In some embodiments, the filter membrane comprises a blot membrane. In some embodiments, the filter membrane comprises a western blot membrane.

In some embodiments, dispensing process fluids comprises adding a blocking buffer to the first washing basin, adding at least one antibody solution to the remaining washing basins. In some embodiments, adding at least one antibody solution to the remaining washing basins may include adding a primary antibody solution to the second washing basin; adding a washing buffer to the third, fourth, and fifth washing basins; adding a secondary antibody solution to the sixth washing basin; and adding a washing buffer to the seventh, eighth, and ninth washing basins.

In some embodiments, the sequence of agitating of a biological sample and moving said biological sample among washing basins may be initiated and terminated using a programmable control unit. In some embodiments, the programmable control unit is a conventional computer system. In some embodiments, the programmable control unit is a handheld personal electronic device.

In some embodiments, the bioprocessing method may be designed for the immunolabeling, rinsing and incubation for a western blot analysis. In such embodiments, a blot membrane, such as by way of example a nitrocellulose or polyvinylidene fluoride (PVDF) membrane, containing the separated proteins is placed in a sample holder that provides for flow of fluid across the sample holder and the membrane without allowing the membrane to stick to any of the walls of the sample holder. Antibody solutions, as well as the appropriate blocking and washing solutions may be added to the designated washing basins of the automated bioprocessing apparatus. The agitating and moving sequence, duration, and solutions used are selected depending on the specific analysis and proteins involved and can be modified by the user.

In some embodiments, the bioprocessing method may be designed for the labeling of a molecule for a blot analysis using a label or tag, such as a fluorescent tag, such as quantum dots or fluorescence dyes, such as Alexa Fluor® dyes. Solutions containing labels may be added to the designated washing basins.

In some embodiments, the bioprocessing method may be designed for the detection of a biomolecule absorbed or supported on a slide. Agitating the slide in processing fluids in different washing basins may comprise a) enhancing the binding of desired biomolecules onto the slide, b) washing away undesired biomolecules from the slide, and c) reacting the desired biomolecules with reagents specific thereto. Targeted biomolecules may include proteins, peptides, polysaccharides, lipids, and glycoproteins, In some embodiments, the bioprocessing method may be designed for the purification and isolation of nucleic acid. In some embodiments, crude nucleic acid may be preloaded onto a silica membrane of a sample holder. In some embodiments, crude nucleic acid may be added to the first washing basin, and a sample holder, which comprises a silica membrane, is then agitated within the first washing basin to ensure sufficient binding of nucleic acid to the silica membrane. Subsequent agitating of sample holders in different washing basins comprises a) washing away undesired biomolecules from the silica membrane, b) washing away inorganic salts from the silica membrane, and c) eluding the nucleic acid from the silica membrane.

In some embodiments, any of the methods of bioprocessing described herein may be stored as a portion of or as a complete bioprocessing protocol on a programmable control unit. In some embodiments, the stored protocol may further include details delineating timing for each step and the sequence of agitating and moving biological samples.

In some embodiments, the user can use buttons on an automated bioprocessing device to select and store a bioprocessing method for the processing of biological samples. In some embodiments, the user can use a programmable control unit to select, store, download, and upload a bioprocessing method for the processing of biological samples.

In some embodiments, the bioprocessing method may comprise reading barcodes at each washing basin of an automated bioprocessing device. Said barcodes encode information such as agitating and moving sequence, duration, and termination for said bioprocessing method. Said automated bioprocessing device further comprises a barcode reader, which is in communication with a control system of said automated bioprocessing device. Said barcode reader reads barcodes specific for each washing basin.

It should be understood that the above process may be modified, including having one or more steps removed, added or the order of one or more steps changed without departing from the scope of the methods described herein.

We claim:

1. An automated bioprocessing device comprising:
a) a housing;
b) a cover;
c) one or more first sample holders, said first sample holder holds one or more biological samples;
d) one or more removable washing basin assemblies on said housing, each washing basin assembly comprising at least 2 washing basins, each washing basin configured to store a processing fluid, each washing basin configured to receive said first sample holder, each washing basin configured to be of the same or different volume;
e) one or more robot assemblies on said housing, each robot assembly configured to transport said first sample holder and said biological samples therein from one said washing basin to another said washing basin, and to agitate said biological samples within said washing basin; and
f) a control system configured to operate said robot assembly according to a predetermined schedule, said control system comprising at least one bioprocessing controller;
wherein said first sample holder is selected from a group consisting of a second sample holder and a third sample holder;
said second sample holder comprises:
   i) a cylinder chamber configured to hold said biological sample;
   ii) a plurality of bumps on an inside surface of said cylinder chamber;
   iii) a cap on an end of said cylinder chamber, said cap configured to connect said second sample holder to said robot assembly; and
   iv) a plurality of first openings on said cylinder chamber and said cap whereby the free flow of said processing fluid is allowed;
and said third sample holder comprises:
   i) a first chamber, said first chamber made from bendable materials and configured to hold said biological samples;
   ii) a plurality of second openings on said first chamber whereby the free flow of said processing fluid is allowed; and
   iii) a rotation reel inside said first chamber, said rotation reel configured to be controlled by said robot assembly to hold and rotate said first chamber.

2. An automated bioprocessing device comprising:
a) a housing;
b) a cover;
c) one or more first sample holders, said first sample holder holds one or more biological samples;
d) one or more removable washing basin assemblies on said housing, each washing basin assembly comprising at least 2 washing basins, each washing basin configured to store a processing fluid, each washing basin configured to receive said first sample holder, each washing basin configured to be of the same or different volume:,
e) one or more first robot assemblies on said housing, each first robot assembly configured to transport said first sample holder and said biological samples therein from one said washing basin to another said washing basin, and to agitate said biological samples within said washing basin; and
f) a control system configured to operate said robot assembly according to a predetermined schedule, said control system comprising at least one bioprocessing controller;
wherein said first robot assembly is selected from a group consisting of a second robot assembly, a third robot assembly, and a fourth robot assembly;
said second robot assembly comprises:
   i) a first translation mechanism connected to said sample holder and configured to reciprocate said sample holder within said washing basin in a first vertical direction relative to said washing basin assembly; and
   ii) a first rotation mechanism connected to said first translation mechanism and configured to move said sample holder around a first central axis parallel to said first vertical direction;

said third robot assembly comprises:
- i) a second rotation mechanism connected to said sample holder and configured to rotate said sample holder within said washing basin; and
- b) a second translation mechanism connected to said second rotation mechanism and configured to move said sample holder in a second horizontal direction relative to said washing basin assembly;

and said fourth robot assembly comprises
- a) a third rotation mechanism connected to said sample holder and configured to rotate said sample holder within said washing basin; and
- b) a fourth rotation mechanism connected to said third rotation mechanism and configured to move said sample holder around a second central axis parallel to a second vertical direction relative to said washing basin assembly.

3. The device of claim 2, wherein said control system further comprises a conventional computer system.

4. The device of claim 2, wherein said control system further comprises a handheld personal electronic device.

5. The device of claim 2, wherein said first robot assembly includes at least one motor.

\* \* \* \* \*